United States Patent
Reijo Pera et al.

(10) Patent No.: US 8,883,430 B2
(45) Date of Patent: Nov. 11, 2014

(54) ENHANCED EFFICIENCY OF INDUCED PLURIPOTENT STEM CELL GENERATION FROM HUMAN SOMATIC CELLS

(75) Inventors: Renee A. Reijo Pera, Palo Alto, CA (US); James Byrne, Santa Monica, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 184 days.

(21) Appl. No.: 13/391,251

(22) PCT Filed: Aug. 18, 2010

(86) PCT No.: PCT/US2010/045933
§ 371 (c)(1),
(2), (4) Date: May 14, 2012

(87) PCT Pub. No.: WO2011/022507
PCT Pub. Date: Feb. 24, 2011

(65) Prior Publication Data
US 2012/0220030 A1     Aug. 30, 2012

Related U.S. Application Data

(60) Provisional application No. 61/276,112, filed on Aug. 21, 2009.

(51) Int. Cl.
*G01N 33/53* (2006.01)
*C12N 5/00* (2006.01)
*C12N 5/08* (2006.01)
*C12N 5/074* (2010.01)

(52) U.S. Cl.
CPC ........ *C12N 5/0696* (2013.01); *C12N 2501/604* (2013.01); *C12N 2501/115* (2013.01); *C12N 2501/602* (2013.01); *C12N 2501/606* (2013.01); *C12N 2501/119* (2013.01); *C12N 2501/603* (2013.01); *C12N 2502/13* (2013.01); *C12N 2500/44* (2013.01)
USPC .............................. 435/7.1; 435/325; 435/372

(58) Field of Classification Search
CPC ........... C12N 5/06; C12N 5/00; C12N 5/0696
See application file for complete search history.

(56) References Cited

U.S. PATENT DOCUMENTS

2011/0070647 A1    3/2011   Dezawa et al.

OTHER PUBLICATIONS

Lowry; et al., "Generation of human induced pluripotent stem cells from dermal fibroblasts", PNAS (Feb. 2008), 105 (8):2883-2888.
Park; et al., "Reprogramming of human somatic cells to pluripotency with defined factors", Nature (Jan. 2008), 451:141-147.
Takahashi; et al., "Induction of Pluripotent Stem Cells from Adult Human Fibroblasts by Defined Factors", Cell (Nov. 2007), 131:861-872.
Aasen; et al. "Efficient and rapid generation of induced pluripotent stem cells from human keratinocytes", Nature Biotechnology, (Nov. 2008), 26(11):1276-1284.
Byrne, "Generation of isogenic pluripotent stem cells", Human Molecular Genetics (Apr. 2008), 17(1):R37-R41.
Dravida; et al. "The transdifferentiation potential of limbal fibroblast-like cells", Developmental Brain Research (Dec. 2005), 160(2)239-251.
Feng; et al. "Molecules that promote or enhance reprogramming of somatic cells to induced pluripotent stem cells", Cell Stem Cell (Apr. 2009), 4(4):301-312.
Liu; et al. "Generation of induced pluripotent stem cells from adult rhesus monkey fibroblasts", Cell Stem Cell (Dec. 2008), 3(6):587-590.
Mali; et al. "Improved efficiency and pace of generating induced pluripotent stem cells from human adult and fetal fibroblasts", Stem Cells (Aug. 2008), 26(8)1998-2005.
O'Malley; et al., "New strategies to generate induced pluripotent stem cells", Current Opinion in Biotechnology (Oct. 2009), 20:516-521.
Takahashi; et al. "Induction of pluripotent stem cells from fibroblast cultures", Nature Protocols (Jan. 2007), 2 (12):3081-3089.
Wernig; et al. "In vitro reprogramming of fibroblasts into a pluripotent ES-cell-like state", Nature (Jul. 2007), 448 (7151):318-324.
Zhou; et al., "Adenoviral gene delivery can reprogram human fibroblasts to induced pluripotent stem cells", Stem Cells (Nov. 2009), 27(11)2667-2674.

*Primary Examiner* — Michail Belyavskyi
(74) *Attorney, Agent, or Firm* — Bozicevic, Field & Francis LLP; Pamela J. Sherwood

(57) ABSTRACT

A substantially pure population of human somatic cells that have enhanced potential to become induced pluripotent stem cells (iPS cells) is provided. Also provided are methods for generating this population of cells and methods for generating iPS cells from this population of cells.

4 Claims, 7 Drawing Sheets

ENHANCED EFFICIENCY OF INDUCED PLURIPOTENT STEM CELL GENERATION FROM HUMAN SOMATIC CELLS

GOVERNMENT RIGHTS

The invention was made with support from the California Institute of Regenerative Medicine under grant No. RL1-00670-1.

CROSS REFERENCE TO RELATED APPLICATIONS

This application is a 371 National Phase Application of PCT/US10/45933 filed Aug. 18, 2010; which claims priority to the filing date of the U. S. Provisional Patent Application Ser. No. 61/276,112 filed Aug. 21, 2009; the disclosures of which are herein incorporated by reference.

FIELD OF THE INVENTION

Human somatic cells are selected for one or more markers associated with pluripotency, to provide a purified population of cells that have enhanced potential to become induced pluripotent stem (iPS) cells.

BACKGROUND OF THE INVENTION

The generation of pluripotent stem cells that are genetically identical to an individual provides unique opportunities for basic research and for potential immunologically-compatible novel cell-based therapies (Byrne J A. (2008) Human Mol. Gen. 17:R37-41). Methods to reprogram primate somatic cells to a pluripotent state include somatic cell nuclear transfer (Stojkovic M, et al. (2005) Reprod Biomed Online 11:226-231; Byrne J A, et al. (2007) Nature 450:497-502), somatic cell fusion with pluripotent stem cells (Cowan C A, et al. (2005) Science 309:1369-1373) and direct reprogramming to produce induced pluripotent stem cells (iPS cells) (Takahashi K, et al. (2007) Cell 131:861-872; Park I H, et al. (2008) Nature 451:141-146; Yu J, et al. (2007) Science 318:1917-1920; Kim D, et al. (2009) Cell Stem Cell 4:472-476; Soldner F, et al. (2009) Cell. 136:964-977; Huangfu D, et al. (2008) Nature Biotechnology 26:1269-1275; Li W, et al. (2009) Cell Stem Cell 4:16-19). These methodologies, however, are characterized by a low reprogramming efficiency and a lack of knowledge regarding the underlying mechanisms. While it has been demonstrated previously that more differentiated cells demonstrate a lower reprogramming efficiency (Gurdon J B and Byrne J A.(2003) Proc Natl Acad Sci U S A 100:8048-8052) and different somatic cell types possess differential reprogramming ability (Aoi T, et al.(2008) Science 321:699-702; Aasen T, et al. (2008) Nature Biotechnology 2008; 26(11):1276-1284) the art has not identified a subpopulation of cells within a somatic cell type possessing differential reprogramming potential.

Isolation of a subpopulation or subpopulations of cells within a somatic cell population possessing differential reprogramming potential would provide a method to significantly increase the efficiency of reprogramming, thereby enhancing the feasibility of the potential applications based on this technology (Byrne J A. (2008) Human Mol. Gen. 17:R37-41). Isolation of such subpopulations would also provide a tool for basic research studies to understand the underlying reprogramming mechanisms.

SUMMARY OF THE INVENTION

A substantially pure population of human somatic cells that have enhanced potential to become induced pluripotent stem (iPS) cells (iPS cells) is provided. Also provided are methods for enriching for a population of human somatic cells that have enhanced potential to become induced pluripotent stem (iPS) cells (iPS cells), for generating iPS cells by using this population of cells, and for using iPS cells generated by this method.

In some aspects of the invention, a substantially pure composition of somatic cells that have an enhanced potential to become iPS cells is provided. The somatic cells with enhanced potential to become iPS cells express of one or more markers associated with pluripotency, and have an increased efficiency of reprogramming relative to somatic cells that do not express the pluripotency marker. In some embodiments of the invention, the pluripotency marker is Stage Specific Embryonic Antigen 3 (SSEA3). Populations of interest include primary cultures of somatic cells, i.e. early passage cells (<10 passages) derived directly from human somatic tissues. In some embodiments, the somatic cells are primary fibroblast cells, including, without limitation, dermal fibroblasts. In some embodiments, the increased efficiency is at least about two-fold or higher.

In some aspects of the invention, methods are provided for enriching or selecting for population of human somatic cells that have enhanced potential to become induced pluripotent stem (iPS) cells (iPS cells). In these methods, a population of somatic cells is contacted with a reagent that specifically recognizes a marker associated with pluripotency, and cells that express the pluripotency marker are selected. In some embodiments, the pluripotency marker is SSEA3. In some embodiments, the initial population of somatic cells that is contacted is population of human fibroblasts. In some such embodiments, the human fibroblasts are dermal fibroblasts. In some embodiments, the initial population of somatic cells is a primary culture.

In some aspects of the invention, methods are provided for generating iPS cells from somatic cells. In these methods, an initial population of somatic cells is contacted with a reagent that specifically recognizes a marker associated with pluripotency, the cells that express the pluripotency marker are selected, and the selected cells are contacted with reprogramming factors. In some embodiments, the pluripotency marker is SSEA3. In some embodiments, the initial population of somatic cells that is contacted is population of human fibroblasts. In some such embodiments, the human fibroblasts are dermal fibroblasts. In some embodiments, the initial population of somatic cells is a primary culture. In some embodiments, the reprogramming factors are provided as viral particles. In some embodiments, the reprogramming factors are provided as nuclear acting, non-integrating polypeptides. In some embodiments, the reprogramming factors include one or more of the following factors: OCT4, SOX2, KLF4, MYC, Nanog, and Lin28. In some embodiments, the reprogramming factors comprise OCT4, SOX2, KLF4 and cMyc.

These and other objects, advantages, and features of the invention will become apparent to those persons skilled in the art upon reading the details of the subject methods and compositions as more fully described below.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
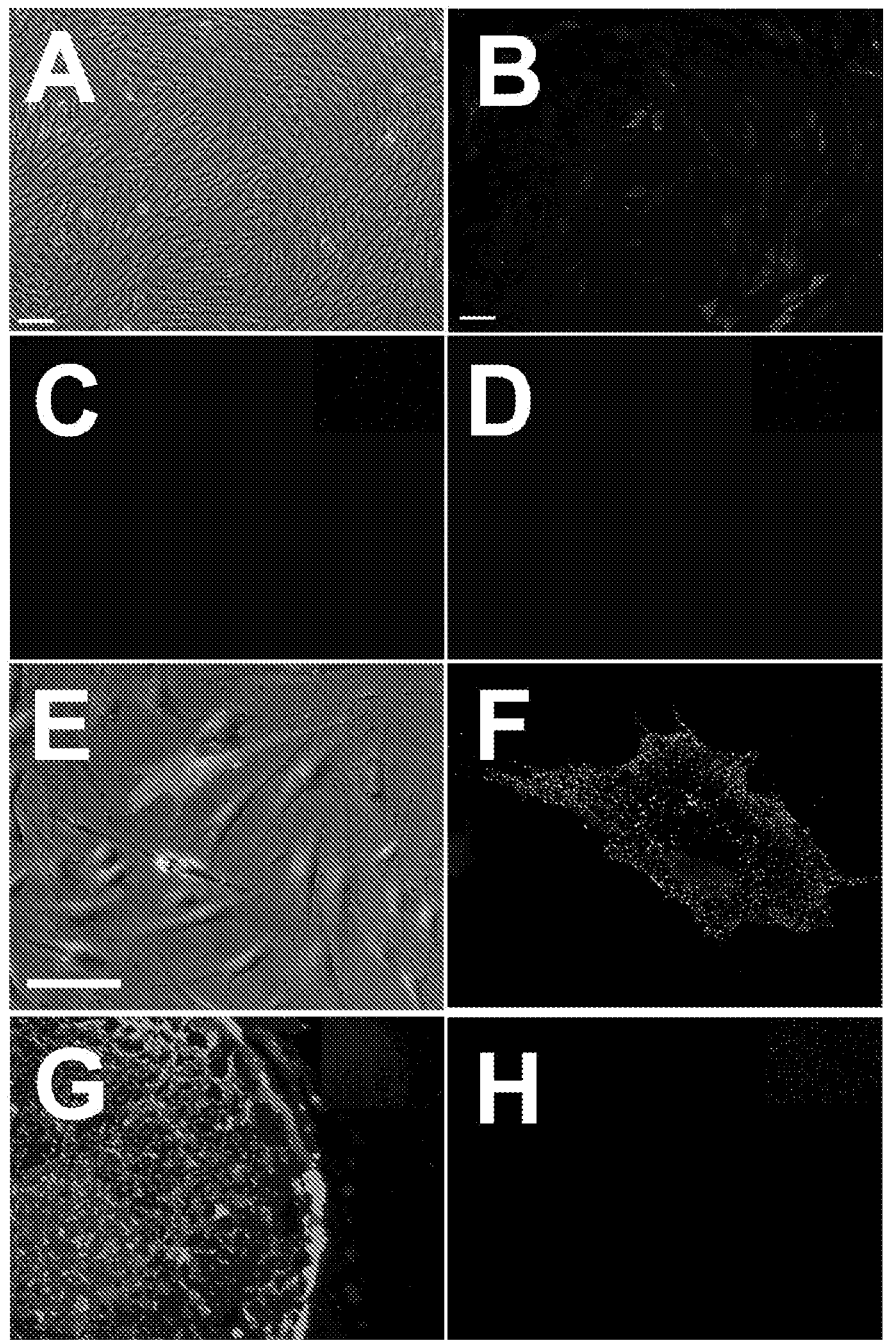
FIG. 1. Expression of SSEA3 from primary human dermal fibroblasts. (A-B) Primary adult human fibroblast line HUF1: (A) Phase contrast image, and (B) Immunocytochemical detection of SSEA3 expression (green). (C-D) Immunofluorescence staining for (C) TRA-1-60 and (D) TRA-1-81 on HUF1 cells. (E) Overlay of SSEA3 expression on phase contrast image of HUF1 cells. (F) Confocal section through primary human fibroblast (HUF1) cell demonstrating SSEA3/488 detection primarily from the cell membrane in addition to localized peri-nuclear detection. (G) SSEA3/488 detection on H9 human embryonic stem cells. (H) 488 secondary antibody only negative control staining of HUF1 cells. (C-H) DAPI staining to label cell nucleic in blue. Scale bars represent 100 microns.

Before the present compositions and methods are described, it is to be understood that this invention is not limited to particular compositions and methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a reprogramming factor polypeptide" includes a plurality of such polypeptides, and reference to "the induced pluripotent stem cells" includes reference to one or more induced pluripotent stem cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

A substantially pure population of human somatic cells that have an enhanced potential to become induced pluripotent stem (iPS) cells (iPSCs) is provided. Also provided are methods for enriching for a population of human somatic cells that have enhanced potential to become induced pluripotent stem (iPS) cells (iPS cells), and methods for generating iPS cells from this population of cells, which may then be used for transplantation, for drug screening, for experimental models of cellular differentiation and interaction; for in vitro screening assays to define growth and differentiation factors, to characterize genes involved in cell development and regulation, and the like. These cells may be used directly for these purposes, or they may be genetically modified to provide altered capabilities. These and other objects, advantages, and features of the invention will become apparent to those persons skilled in the art upon reading the details of the subject methods and compositions as more fully described below.

The terms "differentiated somatic cell" or simply "somatic cell" encompasses any cell in or of an organism that cannot give rise to all types of cells in an organism. In other words, somatic cells are cells that have differentiated sufficiently that they will not naturally generate cells of all three germ layers of the body, i.e. ectoderm, mesoderm and endoderm. For example, somatic cells would include both neurons and neural progenitors, the latter of which may be able to naturally give rise to all or some cell types of the central nervous system but cannot give rise to cells of the mesoderm or endoderm lineages.

The terms "primary cells", "primary cell lines", and "primary cultures" are used interchangeably herein to refer to cells and cells cultures that have been derived from a subject and allowed to grow in vitro for a limited number of passages, i.e. splittings, of the culture. For example primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

By "pluripotency" it is meant the ability of cells to differentiate into all types of cells in an organism. By "pluripotent stem cells", it is meant cells that can a) self-renew and b) differentiate to produce all types of cells in an organism. The term "induced pluripotent stem cell" encompasses pluripotent stem cells, that, like embryonic stem (ES) cells, can be cultured over a long period of time while maintaining the ability to differentiate into all types of cells in an organism, but that, unlike ES cells (which are derived from the inner cell mass of blastocysts), are derived from somatic cells, that is, cells that had a narrower, more defined potential and that in the absence of experimental manipulation could not give rise to all types of cells in the organism. iPS cells have an hESC-like morphology, growing as flat colonies with large nucleo-cytoplasmic ratios, defined borders and prominent nuclei. In addition, iPS cells express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In addition, the iPS cells are capable of forming teratomas. In addition, they are capable of forming or contributing to ectoderm, mesoderm, or endoderm tissues in a living organism.

By "having the potential to become iPS cells" it is meant that somatic cells can be induced to become, i.e. can be reprogrammed to become, iPS cells. In other words, the somatic cell can be induced to redifferentiate so as to establish cells having the morphological characteristics, growth ability and pluripotency of pluripotent cells.

The term "efficiency of reprogramming" is used to refer to the ability of a primary cell culture to give rise to iPS cell colonies when contacted with reprogramming factors. By "enhanced efficiency of reprogramming" it is meant that the cells will demonstrate an enhanced ability to give rise to iPS cells when contacted with reprogramming factors relative to a control.

As used herein, "reprogramming factors" refers to one or more, i.e. a cocktail, of biologically active factors that act on a cell to alter transcription, thereby reprogramming a cell to multipotency or to pluripotency. Reprogramming factors may be provided to the cells of the subject invention individually or as a single composition, that is, as a premixed composition, of reprogramming factors. The factors may be provided at the same molar ratio or at different molar ratios. The factors may be provided once or multiple times in the course of culturing the cells of the subject invention. In some embodiments the reprogramming factor is a transcription factor, including without limitation, Oct3/4; Sox2; Klf4; c-Myc; Nanog; and Lin-28.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," are used interchangeably herein and refer to any mammalian subject for whom diagnosis, treatment, or therapy is desired, particularly humans.

A substantially pure composition of human somatic cells that have enhanced potential to become induced pluripotent stem (iPS) cells (iPSCs) is provided. As discussed above, the term "somatic cell" encompasses any cell in an organism that cannot give rise to all types of cells in an organism, i.e. it is not pluripotent. In other words, somatic cells are cells that have differentiated sufficiently that they will not naturally generate cells of all three germ layers of the body, i.e. ectoderm, mesoderm and endoderm. Examples of somatic cells that may comprise the substantially pure composition of the present application are those from ectodermal (e.g., keratinocytes), mesodermal (e.g., fibroblast), endodermal (e.g., pancreatic cells), or neural crest lineages (e.g. melanocytes). The somatic cells may be, for example, dermal fibroblasts, keratinocytes, pancreatic beta cells, neurons, oligodendrocytes, astrocytes, hepatocytes, hepatic stem cells, cardiomyocytes, skeletal muscle cells, smooth muscle cells, hematopoietic cells, osteoclasts, osteoblasts, pericytes, vascular endothelial cells, schwann cells, and the like. They may be cells that in the absence of experimental manipulation will not proliferate, or if they do, will only be able to give rise to more of their own kind, e.g. terminally differentiated cells; or they may differentiated to the point that they are capable of giving rise to cells of a specific lineage, e.g. adult non-pluripotent multipotent stem cells, e.g. mesenchymal stem cells, neural stem cells, cardiac stem cells, hepatic stem cells, and the like. In some embodiments, the cells will have a phenotype reflective of their differentiated state e.g. markers, cell morphology, and/ or functional characteristics that reflect the differentiated state of the cells, as is well known in the art. As one non-limiting example, the somatic cell may be a cell of the fibroblast lineage. Cells in this lineage include differentiated fibroblasts, e.g. dermal fibroblasts, and less differentiated progenitor cells, e.g. circulating and tissue-derived mesenchymal stem cells; cells from an epithelial-mesenchymal transition, etc. as is well known in the art. Dermal fibroblasts may express vimentin and/or fibroblast surface antigen (FSA), while less-differentiated fibroblasts may express CD34 and/or heat shock protein 47 (HSP47). In addition, fibroblasts have a general "fibroblastic" morphology, which, in general encompasses a branched cytoplasm surrounding an elliptical, speckled nucleus having one or two nucleoli."

In addition to being somatic cells, the cells that have enhanced potential to become induced pluripotent stem (iPS) cells (iPSCs) will express detectable levels of the pluripotency marker stage-specific embryonic antigen 3 (SSEA3). In other words, the somatic cells are positive for SSEA3 expression, i.e. they are SSEA3$^+$ cells. SSEA3, as first described by Shevinsky L H, et al (1982) Cell 3:697-705, is a carbohydrate cell surface antigen present on both cell surface glycolipids and glycopeptides. Antibodies to SSEA3 are commercially available, for example from Millipore, catalog number mab4303.

It will be understood by those of skill in the art that the stated expression levels reflect detectable amounts of the marker protein on the cell surface. A cell that is negative for staining (the level of binding of a marker specific reagent is not detectably different from an isotype matched control) may still express minor amounts of the marker. And while it is commonplace in the art to refer to cells as "positive" or "negative" for a particular marker, actual expression levels are a quantitative trait. The number of molecules on the cell surface can vary by several logs, yet still be characterized as "positive".

The staining intensity of cells can be monitored by flow cytometry, where lasers detect the quantitative levels of fluorochrome (which is proportional to the amount of cell surface marker bound by specific reagents, e.g. antibodies). Flow cytometry, or FACS, can also be used to separate cell populations based on the intensity of binding to a specific reagent, as well as other parameters such as cell size and light scatter. Although the absolute level of staining may differ with a particular fluorochrome and reagent preparation, the data can be normalized to a control.

In order to normalize the distribution to a control, each cell is recorded as a data point having a particular intensity of staining. These data points may be displayed according to a log scale, where the unit of measure is arbitrary staining intensity. In one example, the brightest stained cells in a sample can be as much as 4 logs more intense than unstained cells. When displayed in this manner, it is clear that the cells falling in the highest log of staining intensity are bright, while those in the lowest intensity are negative. The "low" positively stained cells have a level of staining brighter than that of an isotype matched control, but is not as intense as the most brightly staining cells normally found in the population. An alternative control may utilize a substrate having a defined density of marker on its surface, for example a fabricated bead or cell line, which provides the positive control for intensity.

Also provided are methods for separation/enrichment of somatic cells that have enhanced potential to become iPS cells, i.e. SSEA3 somatic cells, referred to hereafter as "the subject SSEA3+cells" The enriched cell population will be a substantially pure population, where by "substantially pure" it is meant having at least about 70%, about 75%, or about 80% of the cells of the population be of the selected phenotype, more usually at least 85% or 90% of the population be of the selected phenotype, and sometimes at least 95% or more of the population be of the selected phenotype, e.g. 95%, 98%, and up to 100% of the population.

In methods of the invention, somatic cells that have enhanced potential to become iPS cells, i.e. SSEA3$^+$ somatic cells, are separated from an initial population of somatic cells ex vivo or in vitro, i.e. outside the body of the individual, and sometimes in culture. This initial population of somatic cells, referred to hereafter as "the subject initial population" is often a complex mixture or a heterogeneous culture of somatic cells. The subject initial population may be obtained from any mammalian species, e.g. human, primate, equine, bovine, porcine, canine, feline, etc. The subject initial population may include fresh or frozen cells, which may be from a neonate, a juvenile or an adult, and from tissues including skin, muscle, bone marrow, peripheral blood, umbilical cord blood, spleen, liver, pancreas, lung, intestine, stomach, and other differentiated tissues. The tissue may be obtained by biopsy or aphoresis from a live donor, or obtained from a dead or dying donor within about 48 hours of death, or freshly frozen tissue, tissue frozen within about 12 hours of death and maintained at below about −20° C., usually at about liquid nitrogen temperature (−190° C.) indefinitely. For isolation of cells from tissue, an appropriate solution may be used for dispersion or suspension of the cells. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

In some embodiments, the SSEA3$^+$ somatic cells, i.e. the subject SSEA3$^+$ cells, are separated from the subject initial population of somatic cells immediately following dispersion or suspension of the cells. In some embodiments, the subject initial population is cultured first to form a heterogeneous culture of cells, for example, a primary culture of fibroblasts, which is then subjected to separation techniques that will enrich for cells that express SSEA3. In some embodiments, the subject initial population is frozen and stored frozen, usually at about −80° C. to about liquid nitrogen temperature (−190° C.), until a time at which the separation of the subject SSEA3$^+$ cells from the subject initial population may be performed. In such cases, the cells are usually stored in 10% DMSO, 50% serum, 40% buffered medium, or some other such solution as is commonly used in the art to preserve cells at such temperatures, and will be thawed and recultured by methods commonly known in the art and as described further below.

Separation of the subject SSEA3$^+$ cells from the subject initial population of somatic cells may be by any convenient separation technique. For example, the subject SSEA3$^+$ cells may be separated from the subject initial population by affinity separation techniques. Techniques for affinity separation may include magnetic separation using magnetic beads coated with an affinity reagent, affinity chromatography, "panning" with an affinity reagent attached to a solid matrix, e.g. plate, cytotoxic agents joined to an affinity reagent or used in conjunction with an affinity reagent, e.g. complement and cytotoxins, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the subject SSEA3+ cells.

To separate the subject SSEA3+ cells by affinity separation techniques, the subject initial population of somatic cells is contacted with an affinity reagent that specifically recognizes and selectively binds the marker associated with pluripotency, i.e. the SSEA3 marker. By "selectively bind" is meant that the molecule binds preferentially to the target of interest or binds with greater affinity to the target than to other molecules. For example, an antibody will bind to a molecule comprising an epitope for which it is specific and not to unrelated epitopes. In some embodiments, the affinity reagent may be an antibody, i.e. an antibody that is specific for SSEA3. In some embodiments, the affinity reagent may be a specific receptor or ligand for SSEA3, e.g. a peptide ligand and receptor; effector and receptor molecules, a T-cell receptor specific for SSEA3, and the like. In some embodiments, multiple affinity reagents specific for SSEA3 may be used. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art. Of particular interest is the use of antibodies as affinity reagents. Conveniently, these antibodies are conjugated with a label for use in separation. Labels include magnetic beads, which allow for direct separation; biotin, which can be removed with avidin or streptavidin bound to a support; fluorochromes, which can be used with a fluorescence activated cell sorter; or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The subject initial population of somatic cells are contacted with the affinity reagent(s) and incubated for a period of time sufficient to bind the available cell surface antigens. The incubation will usually be at least about 5 minutes and usually less than about 60 minutes. It is desirable to have a sufficient concentration of antibodies in the reaction mixture, such that the efficiency of the separation is not limited by lack of antibody. The appropriate concentration is determined by titration, but will typically be a dilution of antibody into the volume of the cell suspension that is about 1:50 (i.e., 1 part antibody to 50 parts reaction volume), about 1:100, about 1:150, about 1:200, about 1:250, about 1:500, about 1:1000, about 1:2000, or about 1:5000. The medium in which the cells are suspended will be any medium that maintains the viability of the cells. A preferred medium is phosphate buffered saline containing from 0.1 to 0.5% BSA or 1-4% goat serum. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, goat serum etc.

The cells in the contacted population that become labeled by the affinity reagent, i.e. the subject SSEA3+ cells, are selected for by any convenient affinity separation technique, e.g. as described above or as known in the art. Following separation, the separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Compositions highly enriched for SSEA3+ somatic cells are achieved in this manner. The SSEA3+ somatic cells will be about 70%, about 75%, about 80%, about 85% about 90% or more of the cell composition, about 95% or more of the enriched cell composition, and will preferably be about 95% or more of the enriched cell composition. In other words, the composition will be a substantially pure composition of SSEA3+ somatic cells. The cells of the substantially pure composition will also express higher levels of the gene Nanog than the cells that express no or low levels of SSEA3 from which they were separated. Additionally, the cells of the substantially pure composition will be morphologically indistinguishable from the cells from which they were separated; for example, if enriched from a human dermal fibroblast population, $SSEA3^+$ somatic cells will appear morphologically substantially the same as or identical to $SSEA3^-$ human dermal fibroblasts.

The SSEA3+ somatic cells, i.e. the subject SSEA3+ cells, may be used immediately. Alternatively, the subject SSEA3+ cells may be frozen at liquid nitrogen temperatures and stored for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

The subject SSEA3+ cells may be cultured in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

The subject SSEA3+ cells may be used in a wide variety of ways. The nutrient medium, which is a conditioned medium, may be isolated at various stages and the components analyzed. Separation can be achieved with HPLC, reversed phase-HPLC, gel electrophoresis, isoelectric focusing, dialysis, or other non-degradative techniques, which allow for separation by molecular weight, molecular volume, charge, combinations thereof, or the like. One or more of these techniques may be combined to enrich further for specific fractions. The subject cells themselves may be analyzed, for example for the expression of genes, for example to better characterize the subject cells.

One preferred use for the subject $SSEA3^+$ cells is to produce iPS cells. To induce the subject $SSEA3^+$ cells to become iPS cells, the substantially pure population of subject $SSEA3^+$ cells, i.e. the population of cells that were selected from the initial population of somatic cells by contacting the initial population with an affinity reagent and selecting for cells that express SSEA3, are contacted with Reprogramming Factors (RFs). Reprogramming factors, as used herein, refers to one or more, i.e. a cocktail, of biologically active factors that act on a cell to alter transcription, thereby reprogramming a cell to multipotency or to pluripotency. In some embodiments the reprogramming factor is a transcription factor, including without limitation, Oct3/4; Sox2; Klf4; c-Myc; Nanog; and Lin-28.

An Oct3/4 polypeptide is a polypeptide comprising an amino acid sequence that is at least 70% identical to the amino acid sequence of human Oct 3/4, also known as Homo sapiens POU class 5 homeobox 1 (POU5F1) the sequence of which may be found at GenBank Accession Nos. NP_002692 and NM_002701. Oct3/4 polypeptides, e.g. those that are at least 70%, 75%, 80%, 85%, 90%, 91%, 92%, 95%, 97%, 99%, or 100% identical to the sequence provided in GenBank Accession No. NM_002701, and the nucleic acids that encode them find use as a reprogramming factor in the present invention.

A Sox2 polypeptide is a polypeptide comprising the amino acid sequence at least 70% identical to the amino acid sequence of human Sox2, i.e., sex-determining region Y-box 2 protein, the sequence of which may be found at GenBank Accession Nos. NP_003097 and NM_003106. Sox2 polypeptides, e.g. those that are at least 70%, 75%, 80%, 85%, 90%, 91%, 92%, 95%, 97%, 99%, or 100% identical to the sequence provided in GenBank Accession No. NM_003106, and the nucleic acids that encode them find use as a reprogramming factor in the present invention.

A Klf4 polypeptide is a polypeptide comprising the amino acid sequence that is at least 70% identical to the amino acid sequence of human Klf4, i.e., Kruppel-Like Factor 4 the sequence of which may be found at GenBank Accession Nos. NP_004226 and NM_004235. Klf4 polypeptides, e.g. those that are at least 70%, 75%, 80%, 85%, 90%, 91%, 92%, 95%, 97%, 99%, or 100% identical to the sequence provided in GenBank Accession No. NM_004235, and the nucleic acids that encode them find use as a reprogramming factor in the present invention.

A c-Myc polypeptide is a polypeptide comprising an amino acid sequence that is at least 70% identical to the amino acid sequence of human c-Myc, i.e., myelocytomatosis viral oncogene homolog, the sequence of which may be found at GenBank Accession Nos. NP_002458 and NM_002467. c-Myc polypeptides, e.g. those that are at least 70%, 75%, 80%, 85%, 90%, 91%, 92%, 95%, 97%, 99%, or 100% identical to the sequence provided in GenBank Accession No. NM_002467, and the nucleic acids that encode them find use as a reprogramming factor in the present invention.

A Nanog polypeptide is a polypeptide comprising an amino acid sequence that is at least 70% identical to the amino acid sequence of human Nanog, i.e., Nanog homeobox, the sequence of which may be found at GenBank Accession Nos. NP_079141 and NM_024865. Nanog polypeptides, e.g. those that are at least 70%, 75%, 80%, 85%, 90%, 91%, 92%, 95%, 97%, 99%, or 100% identical to the sequence provided in GenBank Accession No. NM_024865, and the nucleic acids that encode them find use as a reprogramming factor in the present invention.

A Lin-28 polypeptide is a polypeptide comprising an amino acid sequence that is at least 70% identical to the amino acid sequence of human Lin-28, i.e., Lin-28 homolog of C. elegans, the sequence of which may be found at GenBank Accession Nos. NP_078950 and NM_024674. Lin-28 polypeptides, e.g. those that are at least 70%, 75%, 80%, 85%, 90%, 91%, 92%, 95%, 97%, 99%, or 100% identical to the sequence provided in GenBank Accession No. NM_024674, and the nucleic acids that encode them find use as a reprogramming factor in the present invention.

In some embodiments, reprogramming factors are provided to the substantially pure composition of subject SSEA3$^+$ cells as nucleic acids encoding said reprogramming factors. Many vectors useful for transferring exogenous genes into target mammalian cells are available. The vectors may be maintained episomally, e.g. as plasmids, minicircle DNAs, virus-derived vectors such cytomegalovirus, adenovirus, etc., or they may be integrated into the target cell genome, through homologous recombination or random integration, e.g. retrovirus derived vectors such as MMLV, HIV-1, ALV, etc.

Nucleic acids encoding the reprogramming factors may be provided directly to the subject cells. In other words, the subject SSEA3$^+$ somatic cells are contacted with vectors comprising nucleic acids encoding the reprogramming factors such that the vectors are taken up by the cells. Methods for contacting cells with nucleic acid vectors, such as electroporation, calcium chloride transfection, and lipofection, are well known in the art.

Alternatively, nucleic acids encoding the reprogramming factors may be provided to the subject via a virus. In other words, the subject SSEA3$^+$ somatic cells are contacted with viral particles comprising nucleic acids encoding the reprogramming factors. Retroviruses, for example, lentiviruses, are particularly suitable to the method of the invention, as they can be used to transfect non-dividing cells (see, for example, Uchida et al. (1998) *P.N.A.S.* 95(20):11939-44). Commonly used retroviral vectors are "defective", i.e. unable to produce viral proteins required for productive infection. Rather, replication of the vector requires growth in a packaging cell line.

To generate viral particles comprising nucleic acids encoding the reprogramming factors, the retroviral nucleic acids comprising the nucleic acid encoding the reprogramming factors are packaged into viral capsids by a packaging cell line. Different packaging cell lines provide a different envelope protein to be incorporated into the capsid, this envelope protein determining the specificity of the viral particle for the cells. Envelope proteins are of at least three types, ecotropic, amphotropic and xenotropic. Retroviruses packaged with ecotropic envelope protein, e.g. MMLV, are capable of infecting most murine and rat cell types, and are generated by using ecotropic packaging cell lines such as BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse, and are generated by using amphotropic packaging cell lines such as PA12 (Miller et al. (1985) *Mol. Cell. Biol.* 5:431-437); PA317 (Miller et al. (1986) *Mol. Cell. Biol.* 6:2895-2902); GRIP (Danos et al. (1988) *PNAS* 85:6460-6464). Retroviruses packaged with xenotropic envelope protein, e.g. AKR env, are capable of infecting most mammalian cell types, except murine cells. The appropriate packaging cell line may be used to ensure that the subject CD33+ somatic cells are targeted by the packaged viral particles. Methods of introducing the retroviral vectors comprising the nucleic acid encoding the reprogramming factors into packaging cell lines and of collecting the viral particles that are generated by the packaging lines are well known in the art.

Vectors used for providing reprogramming factors to the subject cells as nucleic acids will typically comprise suitable promoters for driving the expression, that is, transcriptional activation, of the reprogramming factor nucleic acids. This may include ubiquitously acting promoters, for example, the CMV-b-actin promoter, or inducible promoters, such as promoters that are active in particular cell populations or that respond to the presence of drugs such as tetracycline. By transcriptional activation, it is intended that transcription will be increased above basal levels in the target cell by at least about 10 fold, by at least about 100 fold, more usually by at least about 1000 fold. In addition, vectors used for providing reprogramming factors to the subject cells may include genes that must later be removed, e.g. using a recombinase system such as Cre/Lox, or the cells that express them destroyed, e.g. by including genes that allow selective toxicity such as herpesvirus TK, bcl-xs, etc In some embodiments, the reprogramming factors are provided as nuclear acting, non-integrating polypeptides of the reprogramming factors, or reprogramming factor polypeptides. In other words, the subject SSEA3+ somatic cells are contacted with polypeptides that encode the reprogramming factors and act in the nucleus. By non-integrating, it is meant that the polypeptides do not integrate into the genome of the host cell, that is, the subject SSEA3+ somatic cells.

Typically, a reprogramming factor polypeptide will comprise the polypeptide sequences of the reprogramming factor fused to a polypeptide permeant domain. A number of permeant domains are known in the art and may be used in the nuclear acting, non-integrating polypeptides of the present invention, including peptides, peptidomimetics, and non-peptide carriers. For example, a permeant peptide may be derived from the third alpha helix of *Drosophila melanogaster* transcription factor Antennapaedia, referred to as penetratin. As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-96; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002).

The reprogramming factor polypeptide sequences of the reprogramming factor polypeptide may optionally also be fused to a polypeptide domain that increases solubility of the product. Usually the domain is linked to the RF through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase RF solubility, and the like. Domains of interest include endosomolytic domains, e.g. influenza HA domain; and other polypeptides that aid in production, e.g. IF2 domain, GST domain, GRPE domain, and the like.

The reprogramming factor polypeptides may be generated in a cell based system using methods known in the art. A nucleic acid (e.g., cDNA or genomic DNA) encoding the reprogramming factor polypeptide is inserted into a replicable vector for expression. Many such vectors are available. The vector components generally include, but are not limited to, one or more of the following: an origin of replication, one or more marker genes, an enhancer element, a promoter, and a transcription termination sequence.

Reprogramming factor polypeptides may be produced recombinantly not only directly, but also as a fusion polypeptide with a heterologous polypeptide, e.g. a polypeptide having a specific cleavage site at the N-terminus of the mature protein or polypeptide. Expression vectors usually contain a selection gene, also termed a selectable marker. This gene encodes a protein necessary for the survival or growth of transformed host cells grown in a selective culture medium.

Expression vectors will contain a promoter that is recognized by the host organism and is operably linked to the reprogramming factor coding sequence. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known. Both a native reprogramming factor polypeptide promoter sequence and many heterologous promoters may be used to direct expression of a reprogramming factor polypeptide. However, heterologous promoters are preferred, as they generally permit greater transcription and higher yields. Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding Wnt polypeptide. Cells comprising the expression vector are grown under conditions that provide for expression of the desired polypeptide, which is then extracted from the cell ysate by conventional methods.

Alternatively, reprogramming factor polypeptides may be generated in a cell-free system, for example by the methods taught in U.S. application Ser. No. 61/271,000, which is incorporated herein by reference.

Following purification by commonly known methods in the art, the reprogramming factor polypeptides are provided to the subject cells by standard protein transduction methods. In some cases, the protein transduction method includes contacting cells with a composition containing a carrier agent and at least one purified reprogramming factor polypeptide. Examples of suitable carrier agents and methods for their use include, but are not limited to, commercially available reagents such as Chariot™ (Active Motif, Inc., Carlsbad, Calif.) described in U.S. Pat. No. 6,841,535; Bioport® (Gene Therapy Systems, Inc., San Diego, Calif.), GenomeONE (Cosmo Bio Co., Ltd., Tokyo, Japan), and ProteoJuice™ (Novagen, Madison, Wis.), or nanoparticle protein transduction reagents as described in, e.g., U.S. patent application Ser. No. 10/138,593.

Reprogramming factors may be provided to the subject SSEA3+ somatic cells individually or as a single composition, that is, as a premixed composition, of reprogramming factors. The reprogramming factors may be added to the subject cells simultaneously or sequentially at different times. In some embodiments, a set of at least three purified reprogramming factor is added, e.g., an Oct3/4 polypeptide, a Sox2 polypeptide, and a Klf4 polypeptide. In some embodiments, a set of four purified reprogramming factors is provided to the cells e.g., an Oct3/4 polypeptide, a Sox2 polypeptide, a Klf4 polypeptide, and a c-Myc polypeptide. In some embodiments, cells are incubated in the presence of a purified IF polypeptide for about 30 minutes to about 24 hours, e.g., 1 hours, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours. In some embodiments, protein transduction of cells is repeated with a frequency of about every day to about every 4 days, e.g., every 1.5 days, every 2 days, every 3 days, or any other frequency from about every day to about every four days with the same or different IF polypeptides. Typically, the reprogramming factors are provided to the subject cells once, and the cells are allowed to incubate with the reprogramming factors for 16-24 hours, after which time the media is replaced with fresh media and the cells are cultured further, or the reprogramming factors are provided to the subject cells twice, with two 16-24 hour incubations with the recombination factors following each provision, after which the media is replaced with fresh media and the cells are cultured further.

After contacting the subject SSEA3$^+$ somatic cells with the reprogramming factors, the contacted cells are cultured so as to promote the outgrowth of iPS cells. Methods for culturing cells to promote the growth of ES cells, isolating ES cell clones and culturing cells of those ES cell clones so as to promote the outgrowth of ES cells are well known in the art, any of which may be used in the present invention to grow, isolate and reculture the iPS cells from the reprogrammed subject SSEA3$^+$ somatic cells.

iPS cells induced to become such from the subject SSEA3$^+$ somatic cell population have an hESC-like morphology, growing as flat colonies with large nucleo-cytoplasmic ratios, defined borders and prominent nuclei. In addition, the iPS cells express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In addition, the iPS cells are capable of forming teratomas. In addition, they are capable of forming or contributing to ectoderm, mesoderm, or endoderm tissues in a living organism.

Genes may be introduced into the subject SSEA3$^+$ somatic cells or the iPS cells derived therefrom for a variety of purposes, e.g. to replace genes having a loss of function mutation, provide marker genes, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to introduce nucleic acids into the target cells, e.g. electroporation, calcium precipitated DNA, fusion, transfection, lipofection, infection and the like, as discussed above. The particular manner in which the DNA is introduced is not critical to the practice of the invention.

To prove that one has genetically modified the SSEA3$^+$ somatic cells or the iPS cells derived thereform, various techniques may be employed. The genome of the cells may be restricted and used with or without amplification. The polymerase chain reaction; gel electrophoresis; restriction analysis; Southern, Northern, and Western blots; sequencing; or the like, may all be employed. The cells may be grown under various conditions to ensure that the cells are capable of maturation to all of the myeloid lineages while maintaining the ability to express the introduced DNA. Various tests in vitro and in vivo may be employed to ensure that the pluripotent capability of the cells has been maintained.

It is noted here that a benefit of the subject methods is that they provide for a substantially pure population of cells with an enhanced efficiency of reprogramming to become iPS cells. By "enhanced efficiency of reprogramming" it is meant that the cells will demonstrate an enhanced ability to give rise to iPS cells when contacted with reprogramming factors relative to a control. Cells and cell populations that demonstrate an enhanced efficiency of reprogramming have the ability to give rise to iPS cells that is about 150% of the ability of control cells or control cell populations, about 200%, about 300%, about 400%, about 600%, or about 800% of the ability control cells or control cell populations. In other words, the primary cells or primary cell cultures produce about 1.5-fold, about 2-fold, about 3-fold, about 4-fold, about 6-fold or about 8-fold the number of iPS colonies as control primary cells or a control primary cell population, or more. In some cases, the control cells/control cell population does not express a subject pluripotency marker. In some cases, the control population is a population that comprises some cells expressing the subject pluripotency marker, but is not enriched for those cells expressing the pluripotency marker, i.e. only about 2% or less, 5% or less, 7% or less, 10% or less, sometimes 15%, 20%, or 30% or less, occasionally 40%, 50%, 60% or 70% or less of the cells express the pluripotency marker. Typically, the methods of the invention provide for an increased efficiency of reprogramming that is at least about two-fold or higher than the efficiency of reprogramming of the control population.

The iPS cells produced by the above methods may be used for reconstituting or supplementing differentiating or differentiated cells in a recipient. The induced cells may be differentiated into cell-types of various lineages. Examples of differentiated cells include any differentiated cells from ectodermal (e.g., neurons and fibroblasts), mesodermal (e.g., cardiomyocytes), or endodermal (e.g., pancreatic cells) lineages. The differentiated cells may be one or more: pancreatic beta cells, neural stem cells, neurons (e.g., dopaminergic neurons), oligodendrocytes, oligodendrocyte progenitor cells, hepatocytes, hepatic stem cells, astrocytes, myocytes, hematopoietic cells, or cardiomyocytes.

The differentiated cells derived from the induced cells may be terminally differentiated cells, or they may be capable of giving rise to cells of a specific lineage. For example, induced cells can be differentiated into a variety of multipotent cell types, e.g., neural stem cells, cardiac stem cells, or hepatic stem cells. The stem cells may then be further differentiated into new cell types, e.g., neural stem cells may be differentiated into neurons; cardiac stem cells may be differentiated into cardiomyocytes; and hepatic stem cells may be differentiated into hepatocytes.

There are numerous methods of differentiating the induced cells into a more specialized cell type. Methods of differentiating induced cells may be similar to those used to differentiate stem cells, particularly ES cells, MSCs, MAPCs, MIAMI, hematopoietic stem cells (HSCs). In some cases, the differentiation occurs ex vivo; in some cases the differentiation occurs in vivo.

Any known method of generating neural stem cells from ES cells may be used to generate neural stem cells from induced cells, See, e.g., Reubinoff et al., (2001), Nat, Biotechnol., 19(12): 1134-40. For example, neural stem cells may be generated by culturing the induced cells as floating aggregates in the presence of noggin, or other bone morphogenetic protein antagonist, see e.g., Itsykson et al., (2005), Mol, Cell Neurosci., 30(1):24-36. In another example, neural stem cells may be generated by culturing the induced cells in suspension to form aggregates in the presence of growth factors, e.g., FGF-2, Zhang et al., (2001), Nat. Biotech., (19): 1129-1133. In some cases, the aggregates are cultured in serum-free medium containing FGF-2. In another example, the induced cells are co-cultured with a mouse stromal cell line, e.g., PA6 in the presence of serum-free medium comprising FGF-2. In yet another example, the induced cells are directly transferred to serum-free medium containing FGF-2 to directly induce differentiation.

Neural stems derived from the induced cells may be differentiated into neurons, oligodendrocytes, or astrocytes. Often, the conditions used to generate neural stem cells can also be used to generate neurons, oligodendrocytes, or astrocytes.

Dopaminergic neurons play a central role in Parkinson's Disease and other neurodegenerative diseases and are thus of particular interest. In order to promote differentiation into dopaminergic neurons, induced cells may be co-cultured with a PA6 mouse stromal cell line under serum-free conditions, see, e.g., Kawasaki et al., (2000) Neuron, 28(1):3140. Other methods have also been described, see, e.g., Pomp et al., (2005), Stem Cells 23(7):923-30; U.S. Pat. No. 6,395,546, e.g., Lee et al., (2000), Nature Biotechnol., 18:675-679.

Oligodendrocytes may also be generated from the induced cells. Differentiation of the induced cells into oligodendrocytes may be accomplished by known methods for differentiating ES cells or neural stem cells into oligodendrocytes. For example, oligodendrocytes may be generated by co-culturing induced cells or neural stem cells with stromal cells, e.g., Hermann et al. (2004), J Cell Sci. 117(Pt 19):4411-22. In another example, oligodendrocytes may be generated by culturing the induced cells or neural stem cells in the presence of a fusion protein, in which the Interleukin (IL)-6 receptor, or derivative, is linked to the IL-6 cytokine, or derivative thereof. Oligodendrocytes can also be generated from the induced cells by other methods known in the art, see, e.g. Kang et al., (2007) Stem Cells 25, 419-424.

Astrocytes may also be produced from the induced cells. Astrocytes may be generated by culturing induced cells or neural stem cells in the presence of neurogenic medium with bFGF and EGF, see e.g., Brustle et al., (1999), Science, 285: 754-756.

Induced cells may be differentiated into pancreatic beta cells by methods known in the art, e.g., Lumelsky et al., (2001) Science, 292:1389-1394; Assady et al., (2001), Diabetes, 50:1691-1697; D'Amour et al., (2006), Nat. Biotechnol., 24:1392-1401; D'Amour et al., (2005), Nat. Biotechnol. 23:1534-1541. The method may comprise culturing the induced cells in serum-free medium supplemented with Activin A, followed by culturing in the presence of serum-free medium supplemented with all-trans retinoic acid, followed by culturing in the presence of serum-free medium supplemented with bFGF and nicotinamide, e.g., Jiang et al., (2007), Cell Res., 4:333-444. In other examples, the method comprises culturing the induced cells in the presence of serum-free medium, activin A, and Wnt protein from about 0.5 to about 6 days, e.g., about 0.5, 1, 2, 3, 4, 5, 6, days; followed by culturing in the presence of from about 0.1% to about 2%, e.g., 0.2%, FBS and activin A from about 1 to about 4 days, e.g., about 1, 2, 3, or 4 days; followed by culturing in the presence of 2% FBS, FGF-10, and KAAD-cyclopamine (keto-N-aminoethylaminocaproyl dihydro cinnamoylcyclopamine) and retinoic acid from about 1 to about 5 days, e.g., 1, 2, 3, 4, or 5 days; followed by culturing with 1% B27, gamma secretase inhibitor and extendin-4 from about 1 to about 4 days, e.g., 1, 2, 3, or 4 days; and finally culturing in the presence of 1% B27, extendin-4, IGF-1, and HGF for from about 1 to about 4 days, e.g., 1, 2, 3, or 4 days.

Hepatic cells or hepatic stem cells may be differentiated from the induced cells. For example, culturing the induced cells in the presence of sodium butyrate may generate hepatocytes, see e.g., Rambhatla et al., (2003), Cell Transplant, 12:1-11. In another example, hepatocytes may be produced by culturing the induced cells in serum-free medium in the presence of Activin A, followed by culturing the cells in fibroblast growth factor-4 and bone morphogenetic protein-2, e.g., Cai et al., (2007), Hepatology, 45(5): 1229-39. In an exemplary embodiment, the induced cells are differentiated into hepatic cells or hepatic stem cells by culturing the induced cells in the presence of Activin A from about 2 to about 6 days, e.g., about 2, about 3, about 4, about 5, or about 6 days, and then culturing the induced cells in the presence of hepatocyte growth factor (HGF) for from about 5 days to about 10 days, e.g., about 5, about 6, about 7, about 8, about 9, or about 10 days.

The induced cells may also be differentiated into cardiac muscle cells. Inhibition of bone morphogenetic protein (BMP) signaling may result in the generation of cardiac muscle cells (or cardiomyocytes), see, e.g., Yuasa et al., (2005), Nat. Biotechnol., 23(5):607-11. Thus, in an exemplary embodiment, the induced cells are cultured in the presence of noggin for from about two to about six days, e.g., about 2, about 3, about 4, about 5, or about 6 days, prior to allowing formation of an embryoid body, and culturing the embryoid body for from about 1 week to about 4 weeks, e.g., about 1, about 2, about 3, or about 4 weeks.

In other examples, cardiomyocytes may be generated by culturing the induced cells in the presence of leukemia inhibitory factor (LIF), or by subjecting them to other methods known in the art to generate cardiomyocytes from ES cells, e.g., Bader et al., (2000), Circ. Res., 86:787-794, Kehat et al., (2001), J. Clin. Invest., 108:407-414; Mummery et al., (2003), Circulation, 107:2733-2740.

Examples of methods to generate other cell-types from induced cells include: (1) culturing induced cells in the presence of retinoic acid, leukemia inhibitory factor (LIF), thyroid hormone (T3), and insulin in order to generate adipocytes, e.g., Dani et al., (1997), J. Cell Sci., 110:1279-1285; (2) culturing induced cells in the presence of BMP-2 or BMP4 to generate chondrocytes, e.g., Kramer et al., (2000), Mech. Dev., 92:193-205; (3) culturing the induced cells under conditions to generate smooth muscle, e.g., Yamashita et al., (2000), Nature, 408:92-96; (4) culturing the induced cells in the presence of beta-1 integrin to generate keratinocytes, e.g., Bagutti et al., (1996), Dev. Biol., 179:184-196; (5) culturing the induced cells in the presence of Interleukin-3 (IL-3) and macrophage colony stimulating factor to generate macrophages, e.g., Lieschke and Dunn (1995), Exp. Hemat., 23:328-334; (6) culturing the induced cells in the presence of IL-3 and stem cell factor to generate mast cells, e.g., Tsai et al., (2000), Proc. Natl. Acad. Sci. USA, 97:9186-9190; (7) culturing the induced cells in the presence of dexamethasone and stromal cell layer, steel factor to generate melanocytes, e.g., Yamane et al., (1999), Dev. Dyn., 216:450-458; (8) co-culturing the induced cells with fetal mouse osteoblasts in the presence of dexamethasone, retinoic acid, ascorbic acid, beta-glycerophosphate to generate osteoblasts, e.g., Buttery et al., (2001), Tissue Eng., 7:89-99; (9) culturing the induced cells in the presence of osteogenic factors to generate osteoblasts, e.g., Sottile et al., (2003), Cloning Stem Cells, 5:149-155; (10)

overexpressing insulin-like growth factor-2 in the induced cells and culturing the cells in the presence of dimethyl sulfoxide to generate skeletal muscle cells, e.g., Prelle et al., (2000), Biochem. Biophys. Res. Commun., 277:631-638; (11) subjecting the induced cells to conditions for generating white blood cells; or (12) culturing the induced cells in the presence of BMP4 and one or more: SCF, FLT3, IL-3, IL-6, and GCSF to generate hematopoietic progenitor cells, e.g., Chadwick et al., (2003), Blood, 102:906-915.

In some cases, sub-populations of somatic cells may be purified or isolated. In some cases, one or more monoclonal antibodies specific to the desired cell type are incubated with the cell population and those bound cells are isolated. In other cases, the desired subpopulation of cells expresses a reporter gene that is under the control of a cell type specific promoter. In a specific embodiment, the hygromycin B phosphotransferase-EGFP fusion protein is expressed in a cell type specific manner. The method of purifying comprises sorting the cells to select green fluorescent cells and reiterating the sorting as necessary, in order to obtain a population of cells enriched for cells expressing the construct (e.g., hygromycin B phosphotransferase-EGFP) in a cell-type-dependent manner. Selection of desired sub-populations of cells may also be accomplished by negative selection of proliferating cells with the herpes simplex virus thymidine kinase/ganciclovir (HS-Vtk/GCV) suicide gene system or by positive selection of cells expressing a bicistronic reporter, e.g., Anderson et al. (2007) Mol. Ther. (11):2027-2036.

The induced cells, or cells differentiated from the induced cells, may be used as a therapy to treat disease (e.g., a genetic defect). The therapy may be directed at treating the cause of the disease; or alternatively, the therapy may be to treat the effects of the disease or condition. The induced cells may be transferred to, or close to, an injured site in a subject; or the cells can be introduced to the subject in a manner allowing the cells to migrate, or home, to the injured site. The transferred cells may advantageously replace the damaged or injured cells and allow improvement in the overall condition of the subject. In some instances, the transferred cells may stimulate tissue regeneration or repair.

The transferred cells may be cells differentiated from induced cells. The transferred cells also may be multipotent stem cells differentiated from the induced cells. In some cases, the transferred cells may be induced cells that have not been differentiated.

The number of administrations of treatment to a subject may vary. Introducing the induced and/or differentiated cells into the subject may be a one-time event; but in certain situations, such treatment may elicit improvement for a limited period of time and require an on-going series of repeated treatments. In other situations, multiple administrations of the cells may be required before an effect is observed. The exact protocols depend upon the disease or condition, the stage of the disease and parameters of the individual subject being treated.

The cells may be introduced to the subject via any of the following routes: parenteral, intravenous, intraarterial, intramuscular, subcutaneous, transdermal, intratracheal, intraperitoneal, or into spinal fluid.

The induced cells may be differentiated into cells and then transferred to subjects suffering from a wide range of diseases or disorders. Subjects suffering from neurological diseases or disorders could especially benefit from stem cell therapies. In some approaches, the induced cells may be differentiated into neural stem cells or neural cells and then transplanted to an injured site to treat a neurological condition, e.g., Alzheimer's disease, Parkinson's disease, multiple sclerosis, cerebral infarction, spinal cord injury, or other central nervous system disorder, see, e.g., Morizane et al., (2008), Cell Tissue Res., 331(1):323-326; Coutts and Keirstead (2008), Exp. Neurol., 209(2):368-377; Goswami and Rao (2007), Drugs, 10(10):713-719.

For the treatment of Parkinson's disease, the induced cells may be differentiated into dopamine-acting neurons and then transplanted into the striate body of a subject with Parkinson's disease. For the treatment of multiple sclerosis, neural stem cells may be differentiated into oligodendrocytes or progenitors of oligodendrocytes, which are then transferred to a subject suffering from MS.

For the treatment of any neurologic disease or disorder, a successful approach may be to introduce neural stem cells to the subject. For example, in order to treat Alzheimer's disease, cerebral infarction or a spinal injury, the induced cells may be differentiated into neural stem cells followed by transplantation into the injured site. The induced cells may also be engineered to respond to cues that can target their migration into lesions for brain and spinal cord repair, e.g., Chen et al., (2007), Stem Cell Rev., 3(4):280-288.

Diseases other then neurological disorders may also be treated by a stem cell therapy that uses cells differentiated from induced cells, e.g., induced multipotent or pluripotent stem cells. Degenerative heart diseases such as ischemic cardiomyopathy, conduction disease, and congenital defects could benefit from stem cell therapies, see, e.g. Janssens et al., (2006), Lancet, 367:113-121.

Pancreatic islet cells (or primary cells of the islets of Langerhans) may be transplanted into a subject suffering from diabetes (e.g., diabetes mellitus, type 1), see e.g., Burns et al., (2006) Curr. Stem Cell Res. Ther., 2:255-266. In some embodiments, pancreatic beta cells derived from induced cells may be transplanted into a subject suffering from diabetes (e.g., diabetes mellitus, type 1).

In other examples, hepatic cells or hepatic stem cells derived from induced cells are transplanted into a subject suffering from a liver disease, e.g., hepatitis, cirrhosis, or liver failure.

Hematopoietic cells or hematopoietic stem cells (HSCs) derived from induced cells may be transplanted into a subject suffering from cancer of the blood, or other blood or immune disorder. Examples of cancers of the blood that are potentially treated by hematopoietic cells or HSCs include: acute lymphoblastic leukemia, acute myeloblastic leukemia, chronic myelogenous leukemia (CML), Hodgkin's disease, multiple myeloma, and non-Hodgkin's lymphoma. Often, a subject suffering from such disease must undergo radiation and/or chemotherapeutic treatment in order to kill rapidly dividing blood cells. Introducing HSCs derived from induced cells to these subjects may help to repopulate depleted reservoirs of cells.

In some cases, hematopoietic cells or HSCs derived from induced cells may also be used to directly fight cancer. For example, transplantation of allogeneic HSCs has shown promise in the treatment of kidney cancer, see, e.g., Childs et al., (2000), N. Engl. J. Med., 343:750-758. In some embodiments, allogeneic, or even autologous, HSCs derived from induced cells may be introduced into a subject in order to treat kidney or other cancers.

Hematopoietic cells or HSCs derived from induced cells may also be introduced into a subject in order to generate or repair cells or tissue other than blood cells, e.g., muscle, blood vessels, or bone. Such treatments may be useful for a multitude of disorders.

In some cases, the induced cells are transferred into an immunocompromised animal, e.g., SCID mouse, and allowed to differentiate. The transplanted cells may form a mixture of differentiated cell types and tumor cells. The specific differentiated cell types of interest can be selected and purified away from the tumor cells by use of lineage specific markers, e.g., by fluorescent activated cell sorting (FACS) or other sorting method, e.g., magnetic activated cell sorting (MACS). The differentiated cells may then be transplanted into a subject (e.g., an autologous subject, HLA-matched subject) to treat a disease or condition. The disease or condition may be a hematopoietic disorder, an endocrine deficiency, degenerative neurologic disorder, hair loss, or other disease or condition described herein.

The iPS cells may be administered in any physiologically acceptable medium. They may be provided alone or with a suitable substrate or matrix, e.g. to support their growth and/or organization in the tissue to which they are being transplanted. Usually, at least $1 \times 10^5$ cells will be administered, preferably $1 \times 10^6$ or more. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or stromal cells associated with progenitor cell proliferation and differentiation.

Kits may be provided, where the kit will comprise staining reagents that are sufficient to differentially identify the subject SSEA3+ somatic cells described herein. A combination of interest may include one or more reagents specific for the marker or combination of markers of the present invention, and may further include staining reagents specific for other proteins that mark the subject SSEA3+ cells, e.g. Nanog. The staining reagents are preferably antibodies, and may be detectably labeled. Kits may also include tubes, buffers, etc., and instructions for use.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Materials and Methods

Isolation of Primary Adult Dermal Human Fibroblast (HUF) Cell Lines. Nine primary adult dermal human fibroblast (HUF) lines were derived and used in this study. The gender and age of the participants were as follows: HUF1 male 28, HUF2 male 62, HUF3 female 30, HUF4 male 42, HUF5 female 46, HUF6 female 60, HUF7 male 35, HUF8 male 45 and HUF9 female 31. Approval for these somatic derivations and subsequent iPSC generation was obtained from the Stanford University Institutional Review Board and the Stanford University Stem Cell Research Oversight Committee, and informed consent was obtained from each individual participant. For each HUF line derivation, the adult donor was consented and an inner arm 4 mm skin punch biopsy was obtained at the Stanford University Dermatology Clinic by a qualified dermatologist.

The skin biopsies were washed in Ca/Mg-free Dulbecco's Phosphate Buffered Saline (PBS, Invitrogen, Carlsbad, Calif.) and minced into approximately 12 smaller pieces before being seeded onto gelatin-coated 6-well cell culture plates (Corning Enterprises, Corning, N.Y.) containing mouse embryonic fibroblast (MEF) media consisting of Dulbecco's Modified Eagle Medium (DMEM) supplemented with 10% fetal bovine serum (FBS, Invitrogen) and 100 Um! penicillin-streptomycin (Invitrogen), and cultured at 37° C. in a 5% $CO_2$ incubator. The culture medium was partially changed every two days until biopsy adhesion was observed (usually day 4-6) and then completely changed every two days afterwards. Once the fibroblasts migrated out (usually day 10-12) the attached biopsy fragments and connected epithelial cells were manually removed and the fibroblasts were allowed to expand up to 80-90% confluence. This primary culture was passaged through brief exposure to 0.05% trypsin-EDTA (Invitrogen) and seeded onto gelatin coated 175-cm flasks with fresh culture medium. These somatic cells were cultured until they reached 90% confluence and then frozen down in MEF medium supplemented with 10% dimethyl sulphoxide (DMSO, Sigma-Aldrich, St. Louis, http://www.sigmaaldrich.com).

Cell Culture. HUF cells were propagated in MEF media consisting of DMEM (Invitrogen) supplemented with 10% FBS (Invitrogen) and 100 Um! Penicillin-Streptomycin (Invitrogen). When the cells reached about 80-90% confluence, they were briefly treated with 0.05% trypsin-EDTA (Invitrogen) and split at 1:3 ratio into a new dish. Human induced pluripotent stem cells (iPS cells) and H9 human embryonic stem cells (hESCs) were maintained in hESC medium consisting of DMEM/F12 supplemented with 20% Knockout Serum Replacer (KSR, Invitrogen), 2 mM L-glutamine (Invitrogen), 0.1 mM non-essential amino acids (Invitrogen), 0.1 mM β-mercaptoethanol (Millipore, Billerica, Mass., http://www.chemicon.com), 100 IU/ml Penicillin-Streptomycin and 10 ng/ml recombinant human basic fibroblast growth factor (β-FGF, Invitrogen). For passaging, individual colonies were simultaneously cut and scraped off from the plate using a customized hockey-style (half-loop) glass pipette tip and transferred to a mitomycin C (Sigma) inactivated MEF seeded dish containing fresh hESC media. All of the research in this study adhered to the National Academy of Sciences guidelines.

Confocal imaging. Confocal images were collected with a Zeiss LSM510 Meta laser scanning confocal microscope (Carl Zeiss, Jena, Germany) with a Zeiss 63" Plan-Apochromat objective (NA 1.4). For DAPI, excitation was at 405 nm, and a 420-480 nm bandpass filter was used. For Alexa 488, excitation was at 488 nm, and a 505-530 nm bandpass filter was used. Both detector pinholes were set at 1 Airy unit. Sampling was at 0.095 μm/pixel, 12-bits per pixel with a 2.18 μs pixel dwell time.

SSEA3 live cell staining and FACS cell sorting. Approximately 10 million HUF1 cells were trypsinized through a 5 min exposure to 0.05% trypsin-EDTA (Invitrogen), exposed to MEF media to inactivate the trypsin and then washed twice with ice cold PBS +2% goat serum (PBS-G). After the first wash the cells were passed through a 40 micrometer filter to remove cellular clumps. For each wash the cells were centrifuged for 5 min at 80 g, the supernatant was removed and the cells were gently resuspended in ice-cold PBS-G. After the washes the cells were resuspended in a 1.5 ml Eppendorf tube in 1 ml of ice-cold PBS-G containing 1:100 SSEA3 antibody (Millipore, mab4303) and incubated for 45 minutes in the dark at 4° C. with gentle rocking. After primary antibody binding the cells were washed three times with ice-cold PBS-G and then resuspended in a 1.5 ml Eppendorf tube in 1 ml of ice-cold PBS-G containing 1:200 Alexa 488-conjugated goat anti-rat IgM (Invitrogen, A21212) and incubated for 45 minutes in the dark at 4° C. with gentle rocking. After secondary antibody binding the cells were washed three times with ice-cold PBS-G and then resuspended in 2 ml of ice-cold PBS-G, passed again through a 40 micrometer filter and then immediately analyzed and sorted on a FACSAria cell sorter (BD Biosciences, San Jose, Calif., USA) with blue laser excitation (488 nm). Data was analyzed, doublet-exclusion gating was performed and the relevant populations were sorted using BD FACSDiva Software (BD Biosciences). Cells gated within the top 10% for SSEA3 expression were sorted into the "SSEA3-positive" population and cells gated within the bottom 10% for SSEA3 expression were sorted into the "SSEA3-negative" population. Both populations were allowed to adhere, proliferate and recover for 3 days prior to retroviral transduction. Cells used for immunofluorescence analysis were fixed immediately following overnight adherence to remove dead and non-viable cells and cells used for transcriptional analysis were cultured for 6 days prior to analysis.

Retroviral Production, Infection and iPSC Generation. The following plasmids were obtained from Addgene: pMXs-hOCT3/4 (17217), pMXs-hSOX2 (17218), pMXs-hKLF4 (17219), pMXs-hc-MYC (17220), pUMVC (8449) and pVSV-G (8454) (Addgene Inc., Cambridge, Mass., USA). 293FT cells (Invitrogen) were maintained in MEF media supplemented with 0.5 mg/ml Geneticin (Invitrogen) and cultured until reaching 90-95% confluence before transfection. One day prior to transfection, fresh antibiotic-free culture media was added to the cells. For each 175 -cm flask, 293FT cells were transfected with 10 µg of plasmid DNA carrying the transgene (OCT4, SOX2, KLF4 or cMYC) along with 10 µg of the envelope plasmid pVSV-G and 15 µg of the packaging plasmid pUMVC. The transfection was facilitated by 120 ul of Lipofectamine 2000 (Invitrogen) and 15 ml opti-MEM (Invitrogen) for 6 hours and then replaced with 18 ml of fresh MEF medium without antibiotics. After 2 days, the viral supernatant was collected by spinning and passing through a Millex-HV 0.45 um filter unit (Millipore). The viral supernatants were concentrated to 100× by ultracentrifugation (Beckman Coulter, Inc., Fullerton, Calif., USA, http://www.beckman.com) at 17,000 RPM for 2.5 hours at 20° C. and then resuspended overnight at 4° C. in MEF media. These 100× concentrated viral stocks were either used fresh or frozen in aliquots at −80C.

One day before transduction, HUF1 cells were seeded at $10^5$ cells per well of a gelatin coated 6-well plate. On the following day (considered day 0) the concentrated retroviral supernatants were thawed and mixed at a 20× OCT4, 10× SOX2, 10× KLF4, 10× cMYC ratio, supplemented with fresh MEF media up to 2 ml volume (per well) and 8 ng/ml polyprene and then exposed to the HUF1 cells at 37° C. and 5% $CO^2$. After 24 hours (on day 1) the mixed viral supernatant was removed, the cells were washed twice with PBS and then cultured in fresh MEF medium. On day 2 a second transduction was performed at the same viral concentrations. On day 3 the mixed viral supernatant was again removed, the cells were washed twice with PBS and then cultured in fresh MEF medium. Five days post-transduction (day 5), the cells were resuspended with trypsin, counted and seeded onto 10-cm dishes pre-plated with irradiated MEF feeders. $10^5$ transduced HUF1 cells were seeded per biological replicate. After overnight incubation, the MEF medium was replaced with hESC medium, and thereafter, the medium was changed either every day or every other day, as required. hESC-like colonies started to appear among background colonies around 14 days post-transduction. The colonies were manually picked and transferred to 12 or 6-well plates pre-plated with MEF feeders on day 21. Colonies that continued to expand and maintained their hESC-like morphology were further passaged; whereas, those that failed to expand and/or spontaneously differentiated were discarded.

Alkaline Phosphatase Staining and Immunofluorescence. Alkaline Phosphatase (AP) staining was performed for 30 min at room temperature in the dark using the Vector Red Alkaline Phosphatase Substrate Kit I (Vector Laboratories, Burlingame, Calif.), according to the manufacturer's protocol. For immunofluorescence, the cells were fixed in 4% paraformaldehyde/PBS for 20 minutes, washed twice with PBS, and blocked with 4% goat serum in PBS for 30 min, with all procedures performed at room temperature. For Nanog staining, prior to blocking, the cells were permeabilized with 1% Triton-X100 for 1 hour at room temperature. Subsequently, the primary antibodies were added to PBS and incubated overnight at 4° C. with gentle shaking. The next day the cells were washed with PBS before fluorescent-conjugated secondary antibodies were added and incubated for an hour at room temperature. Finally, the cells were rinsed with PBS three times and DAPI was used to label the nuclei. Primary antibodies and their dilutions were used as follows: SSEA3 (1:200, IgM, Millipore, mab4303), SSEA4 (1:200, IgG, Millipore, mab4304), TRA1-60 (1:200, IgM, Millipore, mab4360), TRA1-81 (1:200, IgM, Millipore, mab4381), Nanog (1:100, IgG, Abcam, Cambridge, Mass., USA, ab21603). Secondary antibodies used were: Alexa 594-conjugated goat anti-rat IgM (1:500, Invitrogen, A21213), Alexa 488-conjugated goat anti-rat IgM (1:500, Invitrogen, A21212), Alexa 488-conjugated goat anti-mouse IgM (1:500, Invitrogen, A21042), Alexa 488-conjugated goat anti-mouse IgG (1:500, Invitrogen, A11001), Alexa 594-conjugated goat anti-rabbit IgG (1:500, Invitrogen, A11012).

Karyotyping. Spectral karyotyping (SKY) was performed according to a previously published protocol (Nguyen HN and Reijo Pera R. (2008) Cold Spring Harb. Protoc. 5047). Briefly, cells were treated with 0.03 ug/ml KARYOMAX® COLCEMID® Solution (Invitrogen) overnight, then treated with 0.05% trypsin (Invitrogen) for 5 minutes at 37° C. to re-suspend the cells. The trypsin was inactivated by adding DMEM medium containing 10% FBS. Pre-warmed hypotonic solution containing equal amounts of 0.4% Potassium Chloride and 0.4% Sodium Citrate was slowly added to the cells to enhance swelling at 37° C. for 7 minutes. Carnoy's solution (Methanol:Glacial Acetic Acid, 3:1 ratio) was used to fix the cells for 30 min. The cells were then dropped onto a pre-cleaned slide (Fisher Scientific, Pittsburgh, Pa., USA) and the quality of the metaphase spreads were determined by a phase-contrast microscope. After a few days of aging at room temperature, the slide was hybridized with probes from the SKYPAINTTM DNA kit for human chromosomes (Applied Spectral Imaging, Vista, Calif., USA) for 2 days in a 37° C. humidified chamber. The finished metaphase spreads were visualized and analyzed using the SkyView spectral imaging system (Applied Spectral Imaging).

In Vitro Differentiation to Beating Cardiomyocytes. For embryoid body formation, iPS cells were seeded into ultra low attachment plates (Corning) containing DMEM +20% FBS. After 8 days growing in suspension, the cell aggregates were transferred to gelatin-coated dishes containing the same medium to allow the cells to attach. The medium was changed every 2-3 days for up to 3 weeks or until beating cardiomyocytes were observed.

Teratoma Assay. For each graft, approximately $10^6$ iPS cells were manually harvested, washed and resuspended in a 1.5 ml tube containing 300 ul hESC medium and then injected subcutenously into female SCID mice (Charles River Laboratories International, Inc., Wilmington, Mass., USA). Any visible tumors 4-8 weeks post-transplantation were dissected and fixed overnight with 4% paraformaldehyde/PBS solution. The tissues were then paraffin embedded, sectioned, stained with hematoxylin and eosin, and examined for the presence of tissue representatives of all three germ layers.

RNA Extraction and Real-time PCR Analysis. Total RNA was purified using RNeasy Mini Kit (Qiagen, Valencia, Calif.) according to the manufacturer's instructions. 500 ng of RNA was used in reverse transcription with Superscript III (Invitrogen) and random hexamers. 1.25 µl of cDNA from each sample was mixed with master mix consisting of 5 µl Cells Direct 2× reaction mix (Invitrogen), 2.5 µl 0.2× PPP mix (48 genes, Taqman/Applied Biosystems Inc, Foster City, Calif., USA), 0.5 µl Platinum Taq (Invitrogen) and 0.75 µl TE Buffer. The reactions were pre-amped using a thermo cycler (Applied Biosystems) under the following conditions: 1 cycle at 95 C, 10 minutes and 14 cycles at 95 C, 15 seconds and at 60 C, 4 minutes. Then the reactions were diluted with TE buffer to a final volume of 20 µl. 2.25 µl of the pre-amplification products were used in the downstream real-time PCR analysis using the Biomark Fluidigm system (Fluidigm Corporation, San Francisco, Calif., USA) according to the company's recommendation. The Ct values for each sample and gene were normalized relative to GAPDH, RPLPO and CTNNB1 by qBasePlus (Biogazelle, Zulte, Belgium). The level of gene expression for each sample was compared to the overall average for that gene, across the three different HUF1 subpopulations (SSEA3-negative, SSEA3-intermediate and SSEA3-positive) to produce a relative gene expression value.

Statistical analysis. Analysis of variance (ANOVA) statistical comparisons were performed using Statview Software (SAS Institute, Inc., Cary, N.C., USA) with statistical significance set at 0.05.

Results

We derived a fibroblast line from a skin biopsy from a healthy adult male (HUF1) (FIG. 1A) and used immunohistochemistry to characterize the expression of cell surface markers commonly associated with pluripotent stem cells (FIG. 1B, C and D). Unexpectedly, we observed that, even prior to reprogramming, the HUF1 cell population included cells that were heterogeneous for expression of stage specific embryonic antigen 3 (SSEA3; FIG. 1B). SSEA3 is a cell surface glycosphingolipid generally considered an embryonic/pluripotency marker (Kannagi R, et al. (1983) Embo J. 2:2355-2361; Enver T, et al. (2005) Human Molecular Genetics 14:3129-3140). Overlaying phase contrast and SSEA3 immunofluorescence images revealed that the SSEA3 expression was detected across the entire cell surface (FIG. 1E) and using confocal microscopy we observed that the SSEA3 expression was primarily localized to the cellular membrane (FIG. 1F). Additional small and localized regions of SSEA3 fluorescence were also detected around the peri-nuclear region, possibly reflecting the intracellular processing and packaging of SSEA3 on peri-nuclear endoplasmic reticulum and/or golgi bodies (FIG. 1F). Notably, in positive controls, strong cell surface expression of SSEA3 was observed in H9 human embryonic stem cells (hESCs)(FIG. 1G) and no expression was observed in the negative controls (FIG. 1H).

Figure 2:
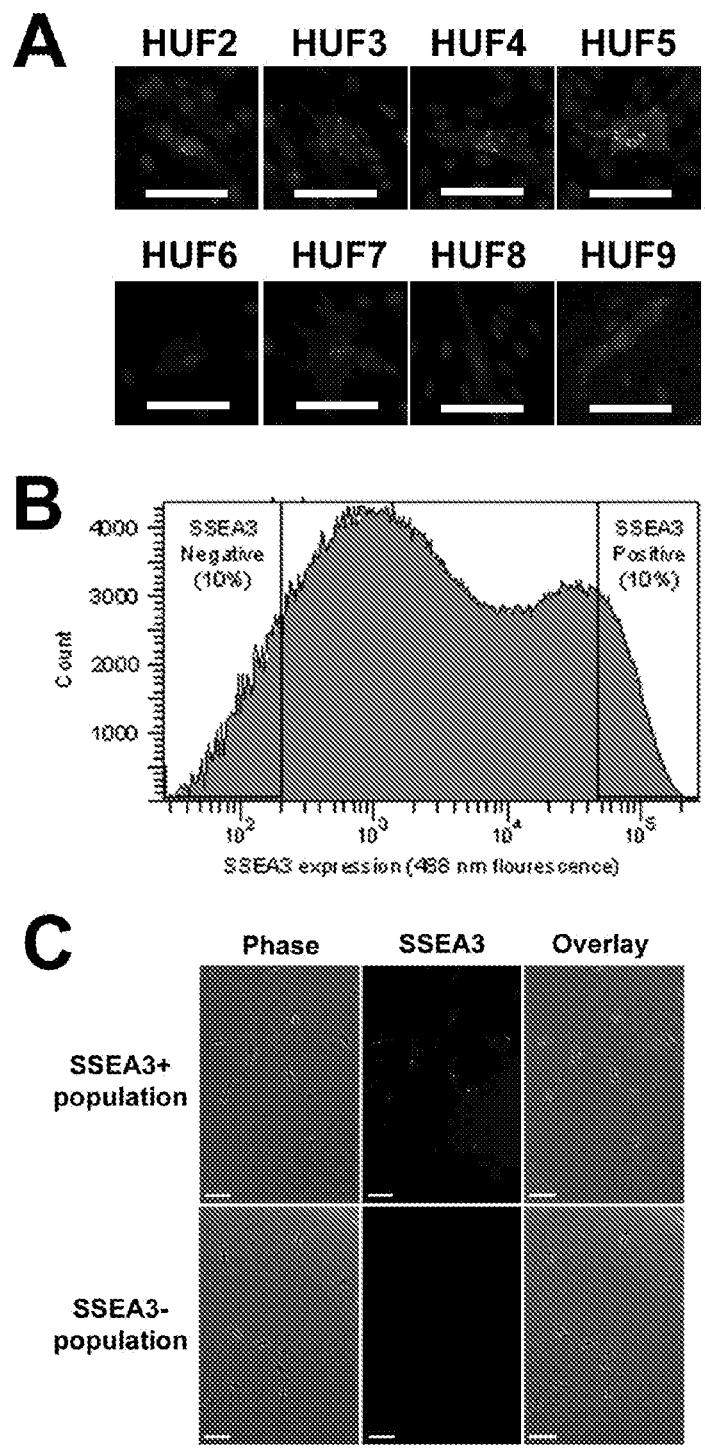
FIG. 2. FACS analysis and isolation of SSEA3-positive primary adult human fibroblasts. (A) Immunocytochemical analysis for SSEA3 expression in eight additional primary adult human dermal fibroblast lines. (B) Histogram of FACS analyzed HUF1 cells following live binding of SSEA3/488 antibody complex. (C) Detection of SSEA3/488 fluorescence signal in FACS sorted SSEA3-positive and SSEA3-negative populations following overnight adherence. SSEA3 staining in green. DAPI staining in blue. Scale bars represent 100 microns.

We next examined whether the expression of SSEA3 in a subset of fibroblasts was specific to HUF1 or a more-general observation. Eight additional primary adult human fibroblast lines were derived from skin biopsies and immunostained. We observed that all eight lines contained a subpopulation of cells that were positive for SSEA3 (FIG. 2A). Fluorescence activated cell sorting (FACS) analysis of HUF1 cells stained with the SSEA3/488 antibody complex, revealed a larger subpopulation of cells with little or no SSEA3 expression and a smaller subpopulation with detectable SSEA3 expression (FIG. 2B). Subsequently, we isolated (through FACS) and cultured the top 10% and bottom 10% of the SSEA3/488 fluorescing cells as our SSEA3-positive and negative populations respectively (FIG. 2B). Immunofluorescence analysis of the two populations, following overnight adherence to exclude analysis of non-viable cells, revealed that >97% of the SSEA3-positive population expressed detectable SSEA3/488 fluorescence and 0% of the SSEA3-negative population expressed detectable SSEA3/488 fluorescence (FIG. 2C), demonstrating that the fluorescence activated cell sorting process can purify viable subpopulations of cells from a heterogeneous somatic population. These subpopulations were then used for reprogramming to iPS cells.

Figure 3:
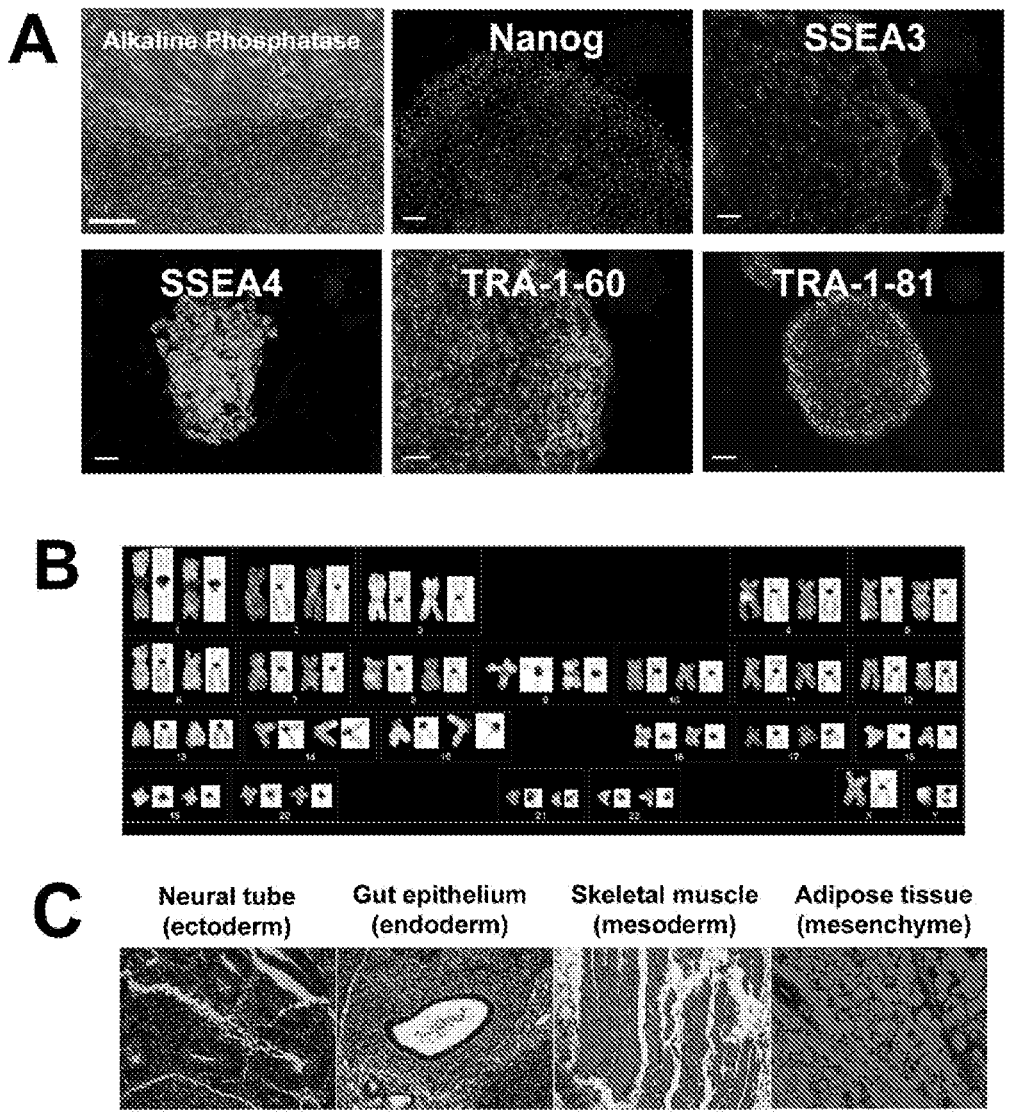
FIG. 3. Characterization of HUF1 derived induced pluripotent stem cells (HiPS-1 control). (A) Expression of pluripotency markers from iPS cells (HiPSC-1 control) generated following retroviral transduction of unsorted HUF1 cells. DAPI staining to label cell nucleic in blue. Scale bar represents 100 microns. (B) SKY karyotype analysis of the HiPS-1 control line. (C) Histological analysis of teratoma from HiPS-1 control line.

Previous reprogramming work demonstrated that we could reprogram the entire, unsorted population of HUF1 somatic cells using retroviral vectors that express OCT4, SOX2, KLF4 and cMYC to generate iPS cells that express the same pluripotency markers as control H9 ESCs (FIG. 3A). Reprogrammed cells possessed a normal karyotype (FIG. 3B) and differentiated in vitro into beating cardiomyocytes, as well as, into representatives of all three germ layers in vivo (FIG. 3C).

Figure 4:
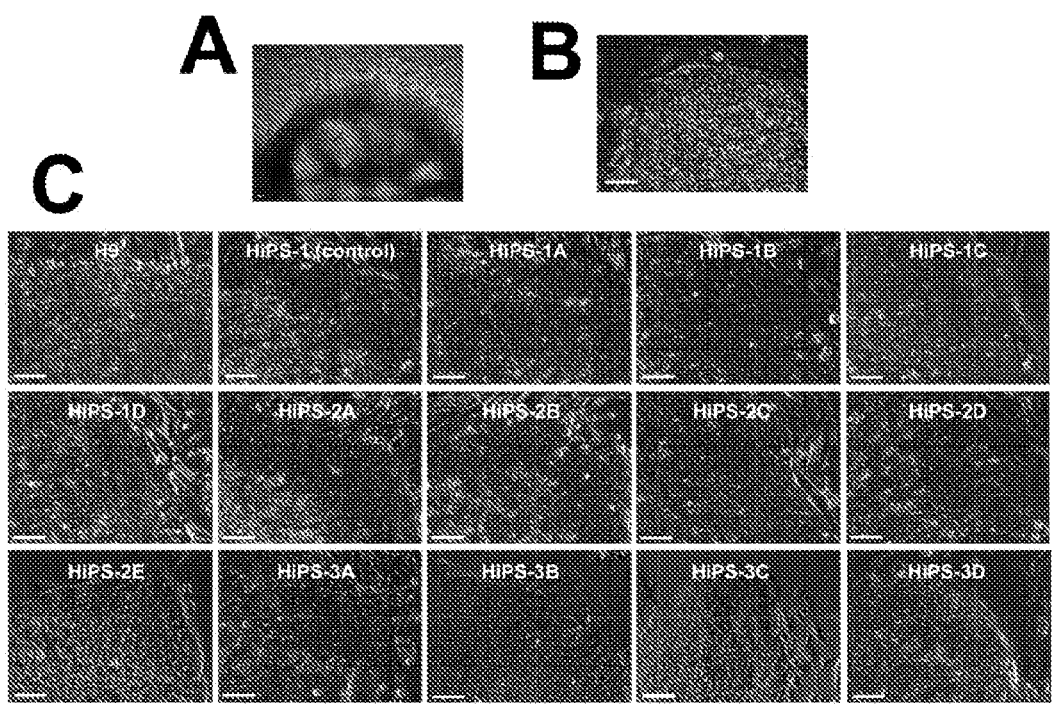
FIG. 4. Morphology of colonies and lines following retroviral transduction of HUF1 cells. (A) Large background colony with no ESC-like attributes. (B) ESC-like iPSC colony. (C) Morphology of SSEA3-selected lines following derivation. (A-C) Scale bar represents 100 microns.

We transduced our SSEA3-positive and SSEA3-negative populations with the same retroviral vectors, under identical experimental conditions, and seeded the transduced cells onto inactivated mouse embryonic fibroblasts (MEFs). After three weeks of culture under standard hESC conditions, plates were examined in a double-blind analysis by three independent hESC biologists for iPSC colony formation. Colonies with iPSC morphology were picked and expanded. We observed that all three biological replicates with the transduced SSEA3-negative cells formed many large background colonies (10-27 per replicate, FIG. 4A) but no iPSC colonies emerged; in contrast, all three biological replicates with the transduced SSEA3-positive cells resulted in the formation of iPSC colonies (4-5 per replicate, FIG. 4B) but very few large background colonies (0-1 per replicate, Table 1). Further characterization of the cell lines derived from the iPSC-like colonies revealed that they possessed hESC-like morphology, growing as flat colonies with large nucleo-cytoplasmic ratios, defined borders and prominent nucleoli (FIG. 4C).

Figure 5:
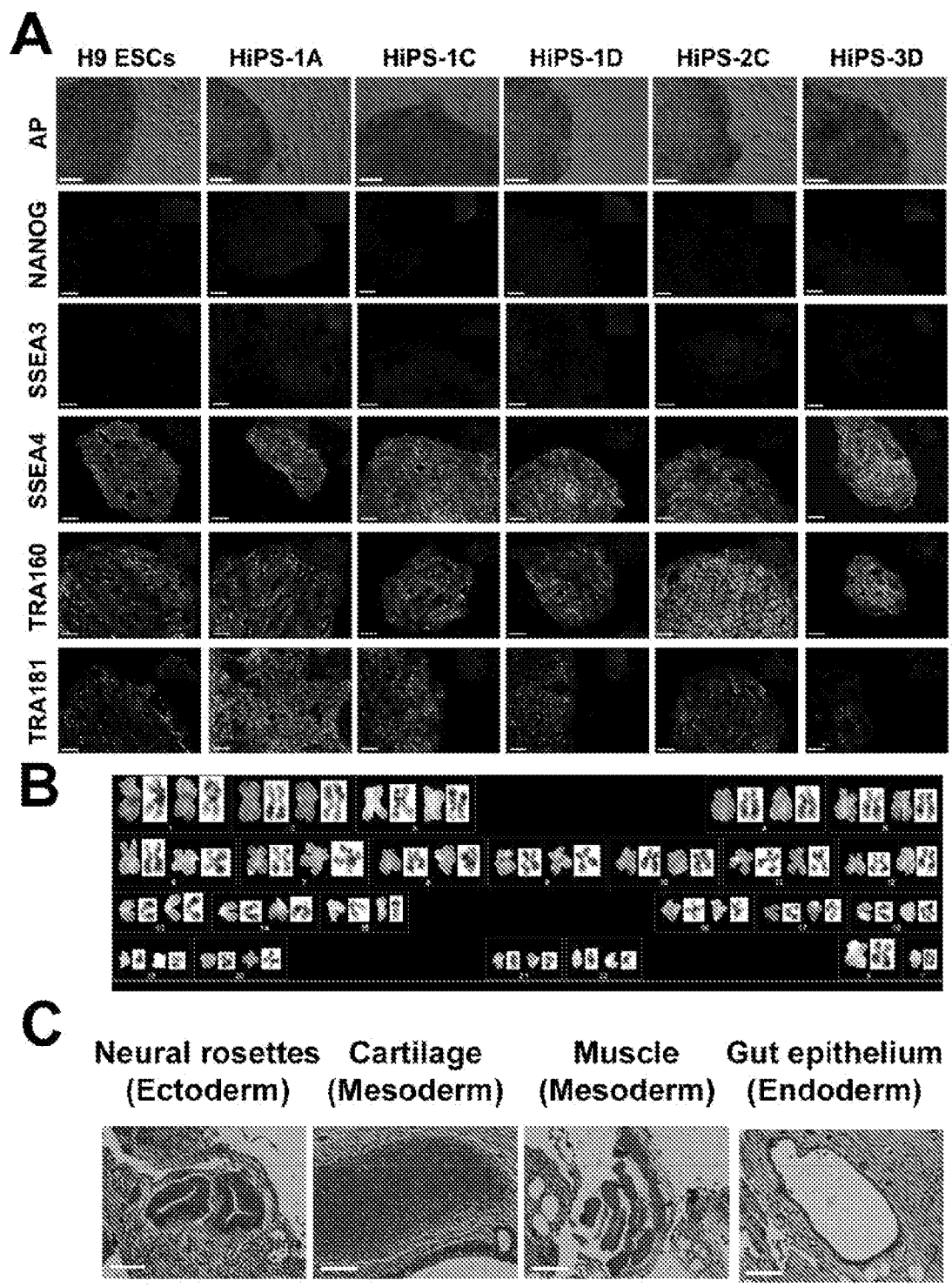
FIG. 5. Pluripotency marker expression and karyotype of SSEA3-selected HiPSC lines. (A) Expression of pluripotency markers on H9 ESCs and SSEA3-selected HiPSC lines. Alkaline phosphatase (AP) staining in dark red/purple. DAPI stained images are inset in blue. Scale bar represents 100 microns. (B) Spectral karyotype (SKY) of SSEA3-selected iPSC line (HiPS-2C). (C) Histological analysis of teratoma from SSEA3-selected iPSC line (HiPSC-2C).

When 5 lines were further expanded and characterized, all demonstrated expression of key pluripotency markers expressed by hESCs, which included: alkaline phosphatase, Nanog, SSEA3, SSEA4, TRA160 and TRA181 (FIG. 5A). The SSEA3-selected iPS cells also demonstrated a normal male karyotype (46, XY)(FIG. 5B), the ability to differentiate into functional beating cardiomyocytes, as well as, into representatives of all three germ layers in vivo (FIG. 5C). Most importantly, since we observed no iPSC colony formation or line derivation from the transduced SSEA3-negative cells, this suggests that these cells possess significantly lower or even no reprogramming potential relative to the SSEA3-expressing cells (Table 1). Additionally, a 10-fold enrichment of primary fibroblasts that strongly express SSEA3 resulted in a significantly greater efficiency (8-fold increase) of iPSC line derivation compared to the control derivation rate ($p<0.05$, Table 1).

TABLE 1

Derivation of human iPS cells from SSEA3 sorted primary dermal fibroblasts

| SSEA3 expression | Biological replicate | iPSC colony formation | iPSC lines derived | Derivation efficiency* |
|---|---|---|---|---|
| Control (unsorted cells) | 1 | 0 | 0 | N/A |
| Control (unsorted cells) | 2 | 1 | 1 | N/A |
| SSEA3-negative cells | 1 | 0 | 0 | 0% |
| SSEA3-negative cells | 2 | 0 | 0 | 0% |
| SSEA3-negative cells | 3 | 0 | 0 | 0% |
| SSEA3-positive cells | 1 | 4 | 4 | 800% |
| SSEA3-positive cells | 2 | 5 | 4** | 800% |
| SSEA3-positive cells | 3 | 4 | 4 | 800% |

*Calculated as percentage compared to control derivation
**HiPS-2E line demonstrated impaired proliferation and is thus not included.
Each biological replicate represented 100,000 transduced cells seeded onto a 10 cm dish containing MEFs and cultured in hESC media for 3 weeks.

Figure 6:
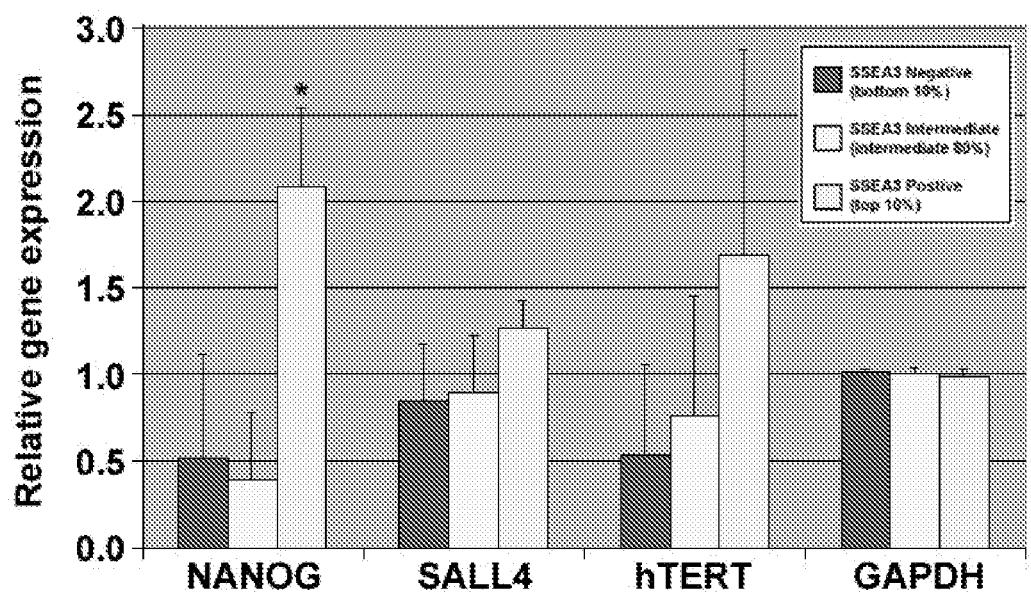
FIG. 6. Transcriptional analysis of primary dermal fibroblast subpopulations with differential SSEA3 expression. Relative expression of Nanog, Sall4, hTert and Gapdh from three subpopulations of HUF1 cells: SSEA3-negative cells (representing the bottom 10% for SSEA3 expression/detection), SSEA3 intermediate cells (representing the intermediate 80% of cells between the top and bottom 10% for expression/detection) and SSEA3-positive cells (representing the top 10% for SSEA3 expression/detection). Three biological replicates were analyzed for each sample. The relative gene expression value represents the level of gene expression for each sample compared to the overall average for that gene across the three subpopulations.
Figure 7:
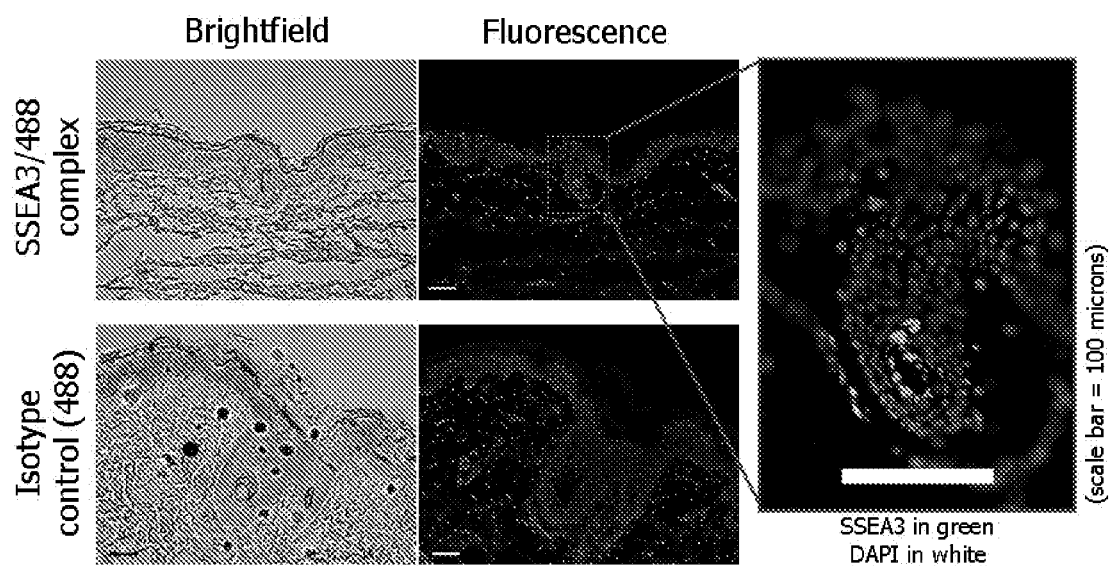
FIG. 7. Expression of SSEA3 in adult human dermal skin biopsy. A subpopulation of cells was detected inside of a structure in the papillary dermis of adult human dermal skin that demonstrated significant fluorescence after exposure to the rat anti-SSEA3 primary antibody and the goat anti-rat 488 secondary antibody. No significant fluorescence was detected from similar structures only exposed to the goat anti-rat secondary antibody (the isotype control). SSEA3 expression is in green and DAPI in white. Scale bar represents 100 microns.

We next examined the expression of genes that might potentially confer the enhanced reprogramming to the SSEA3-positive population, including Nanog (Silva J, et al. (2006) Nature 441:997-1001), Sall4 (Wong C C, et al. (2008) PLoS ONE 3:e1955) and hTert (Park I H, et al. (2008) Nature 451:141-146) as well as several control housing keeping genes (Gapdh, Rplpo and Ctnnb1). In addition to the SSEA3-positive and -negative populations of cells, which represented the top 10% and bottom 10% of SSEA3 expression cells respectively, we also included the intermediary SSEA3-expressing cells, which represented the remaining 80% of the total HUF1 cell population. Three biological replicates for each of the three subpopulations were analyzed. While no significant differences in gene expression were observed for Sall4, hTert or the housekeeping genes (FIG. 6 and table 2), the analysis revealed that expression of Nanog was significantly increased (p<0.05) in the SSEA3-positive cell population compared to either the SSEA3-intermediate or SSEA3-negative population (FIG. 6 and table 2).

TABLE 2

Transcriptional analysis of SSEA3-positive and negative HUF1 cells

| Samples | NANOG CNRQ | SALL4 CNRQ | hTERT CNRQ | GAPDH CNRQ | RPLPO CNRQ | CTNNB1 CNRQ |
|---|---|---|---|---|---|---|
| SSEA3-positive Rep1 | 0.06 | 0.08 | 0.31 | 1.19 | 0.81 | 1.04 |
| SSEA3-positive Rep2 | 0.06 | 0.09 | 0.08 | 1.16 | 0.85 | 1.02 |
| SSEA3-positive Rep3 | 0.04 | 0.07 | 0.49 | 1.28 | 0.90 | 0.87 |
| SSEA3-interm. Rep1 | 0.01 | 0.04 | 0.08 | 1.19 | 0.89 | 0.94 |
| SSEA3-interm. Rep2 | 0.02 | 0.05 | 0.05 | 1.25 | 0.92 | 0.87 |
| SSEA3-interm. Rep3 | 0.00 | 0.08 | 0.27 | 1.27 | 0.89 | 0.89 |
| SSEA3-negative Rep1 | 0.01 | 0.03 | 0.10 | 1.21 | 0.84 | 0.98 |
| SSEA3-negative Rep2 | 0.03 | 0.07 | 0.0 | 1.25 | 0.72 | 1.11 |
| SSEA3-negative Rep3 | 0.00 | 0.06 | 0.18 | 1.26 | 0.74 | 1.07 |
| HiPS1A-SSEA3 sel. | 1828.57 | 103.70 | 40.61 | 0.68 | 1.59 | 0.93 |
| HiPS1-control | 803.45 | 158.54 | 58.55 | 0.49 | 1.56 | 1.30 |
| H9 control ESCs | 1047.77 | 102.25 | 161.29 | 0.41 | 1.60 | 1.51 |

Cells were sorted for SSEA3 and three populations were analyzed after 6 days in culture.
Cells were trypsinized, RNA extracted, cDNA made, preamped and fluidigm analyzed.
Calibrated Normalized Relative Quantity (CNRQ) gene expression level obtained through normalization with CTNNB1, GAPDH and RPLPO.
SSEA3-positive biological replicates (Rep) obtained from top 10% of SSEA3-expressing cells.
SSEA3-interm. (intermediate) replicates obtained from SSEA3-intermediate population.
SSEA3-negative biological replicates obtained from bottom 10% of SSEA3-expressing cells.
HiPS1A-SSEA3 sel. sample represents human iPS cells derived from SSEA3-positive HUF1 cells.
HiPS1-control sample represents human iPS cells derived from unsorted HUF1 cells.

Discussion

In this study, we unexpectedly observed that SSEA3, a cell surface marker normally associated with pluripotent cells, is strongly expressed in a sub-population of cells derived from a primary human dermal fibroblast biopsy. The SSEA3-positive cells appeared indistinguishable, morphologically, from the SSEA3-negative fibroblasts (FIG. 2C). Expression of the SSEA3 antigen is not considered a marker of other multipotent stem cells, e.g. mesenchymal or epidermal adult stem cells (Deans R J and Moseley A B. (2000) Exp Hematol 28:875-884; Lavker R M and Sun T T. (2000) Proc Natl Acad Sci U S A. 97:13473-13475).

Several recent studies have demonstrated that human iPS cells can be generated without permanent integration of genetic factors into the reprogrammed cell chromatin (Kim D, et al. (2009) Cell Stem Cell 4:472-476; Soldner F, et al. (2009) Cell 136:964-977; Kaji K, Norrby K, Paca A, et al. (2009) Nature 458:771-775; Woltjen K, et al. (2009) Nature 458:766-770; Yu J, et al. (2009) Science 324:797-801). While these integration-free human iPS cells hold great promise for future patient specific cell-based therapies (Byrne J A. (2008) Human Mol. Gen. 17:R37-41), the reprogramming efficiency is typically very low. Methods to enhance the reprogramming efficiency will significantly increase the feasibility of this approach, especially for cell types which are difficult to reprogram, such as the primary adult human fibroblasts used in this study. Our control iPSC derivation efficiency using the HUF1 line was very low, with only 1 iPSC line derived from 200,000 cells. However, in this study we have demonstrated that a 10-fold purification of the top SSEA3-expressing cells could increase the efficiency of reprogramming 8-fold relative to unsorted cells and to a much greater extent relative to the SSEA-negative cells. Indeed, in addition to identifying a cell population with enhanced reprogramming efficiency, we also identified an SSEA3-negative population with either significantly reduced reprogramming efficiency or no reprogramming ability. Comparison analysis between the SSEA3-positive and negative populations may help us elucidate the currently poorly understood mechanisms of reprogramming.

Our transcriptional analysis of the SSEA3-positive and -negative populations revealed a significantly increased expression of Nanog in the SSEA3-positive population (p<0.05). As increased Nanog expression has been demonstrated to enhance reprogramming efficiency (Silva J, et al. (2006) Nature 441:997-1001), this suggests Nanog may be playing a role in the differential reprogramming observed. However, it should be noted that the level of Nanog expression is thousands of times higher in hESCs and fully reprogrammed iPS cells than in the SSEA3-expressing HUF1 cells, making it likely that other factors may also be playing a role in the differential reprogramming observed. Future studies using global transcriptional and epigenetic profiling should assist in further identifying the differences between the SSEA3-positive and negative subpopulations, and may help elucidate the mechanisms of reprogramming.

Summary

In summary, we have reported the identification and isolation of a subpopulation of human dermal fibroblasts that express the pluripotency marker SSEA3, we have demonstrated an enhanced efficiency of generation of iPS cells from these SSEA3-expressing cells and observed no iPSC generation from the non-SSEA3-expressing cells, and we have revealed significantly increased Nanog expression in the SSEA3-expressing fibroblasts, suggesting a possible mechanistic explanation for the differential reprogramming. This study is the first to identify a pluripotency marker in a heterogeneous population of human dermal fibroblasts, to isolate a subpopulation of cells that have a significantly increased propensity to reprogram to pluripotency and to identify a mechanism to explain this differential reprogramming.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of enriching for a population of somatic cells that have enhanced potential to become induced pluripotent stem cells (iPS cells), the method comprising:
    contacting an initial population of somatic cells with a reagent that specifically recognizes stage-specific embryonic antigen 3 (SSEA3);
    selecting for cells that express the marker associated with pluripotency to provide a population of somatic cells that have enhanced potential to become iPS cells.

2. The method of claim 1, wherein the somatic cells are human fibroblasts.

3. The method of claim 2, wherein the human fibroblasts are dermal fibroblasts.

4. The method of claim 3, wherein the initial population is a primary in vitro culture.

* * * * *